US012715879B2

(12) United States Patent
Childress et al.

(10) Patent No.: US 12,715,879 B2
(45) Date of Patent: Aug. 25, 2026

(54) QUINAZOLINE-4(3H)-ONE DERIVATIVES AS NEGATIVE ALLOSTERIC MODULATORS OF METABOTROPIC GLUTAMATE RECEPTOR 2

(71) Applicant: Vanderbilt University, Nashville, TN (US)

(72) Inventors: Elizabeth S. Childress, Nashville, TN (US); Craig W. Lindsley, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 425 days.

(21) Appl. No.: 18/553,406

(22) PCT Filed: Apr. 1, 2022

(86) PCT No.: PCT/US2022/023010
§ 371 (c)(1),
(2) Date: Sep. 29, 2023

(87) PCT Pub. No.: WO2022/212815
PCT Pub. Date: Oct. 6, 2022

(65) Prior Publication Data

US 2024/0199641 A1 Jun. 20, 2024

Related U.S. Application Data

(60) Provisional application No. 63/170,244, filed on Apr. 2, 2021.

(51) Int. Cl.

| | |
|---|---|
| ***C07D 498/04*** | (2006.01) |
| ***A61K 31/517*** | (2006.01) |
| ***A61K 31/5383*** | (2006.01) |
| ***C07D 403/12*** | (2006.01) |
| ***C07D 403/14*** | (2006.01) |

(52) U.S. Cl.
CPC .......... *C07D 498/04* (2013.01); *A61K 31/517* (2013.01); *A61K 31/5383* (2013.01); *C07D 403/12* (2013.01); *C07D 403/14* (2013.01)

(58) Field of Classification Search
None
See application file for complete search history.

(56) References Cited

U.S. PATENT DOCUMENTS 10,538,491 B2 1/2020 Conn et al.

FOREIGN PATENT DOCUMENTS

| | | | |
|---|---|---|---|
| JP | 2013189395 | A | 9/2013 |
| WO | 2011116356 | A2 | 9/2011 |
| WO | 2013033246 | A2 | 3/2013 |
| WO | 2020021064 | A1 | 1/2020 |

OTHER PUBLICATIONS

Ma et al (European J Med Chem 207:112723, 2020) (Year: 2020).*
International Search Report and Written Opinion for Application No. PCT/US2022/023010 dated Jun. 22, 2022 (16 pages).
Ma, Y., et al. "Nonpeptidic quinazolinone derivatives as dual nucleotide-binding oligomerization domain-like receptor 1/2 antagonists for adjuvant cancer chemotherapy." European Journal of Medicinal Chemistry 207 (2020): 112723 (19 pages).
Olivero, G., et al. "5-HT2A-mGlu2/3 receptor complex in rat spinal cord glutamatergic nerve endings: A 5-HT2A to mGlu2/3 signalling to amplify presynaptic mechanism of auto-control of glutamate exocytosis." Neuropharmacology 133 (2018): 429-439.

* cited by examiner

*Primary Examiner* — Craig D Ricci
(74) *Attorney, Agent, or Firm* — MICHAEL BEST & FRIEDRICH LLP

(57) ABSTRACT

Described are 6-aryl quinazolin-4(3H)-ones as negative allosteric modulators of metabotropic glutamate receptor 2 ($mGlu_2$), pharmaceutical compositions including the compounds, and methods of using the compounds and compositions for treating depression, anxiety, obsessive-compulsive disorder, cognitive disorders, Alzheimer's disease, or autism spectrum disorders in a subject.

15 Claims, No Drawings

QUINAZOLINE-4(3H)-ONE DERIVATIVES AS NEGATIVE ALLOSTERIC MODULATORS OF METABOTROPIC GLUTAMATE RECEPTOR 2

RELATED APPLICATIONS

This patent application is the U.S. national stage entry, under 35 U.S.C. § 371, of International Application Number PCT/US2022/023010, filed Apr. 1, 2022, which claims priority to U.S. Provisional Application No. 63/170,244, filed Apr. 2, 2021, the entire contents of each of which are hereby incorporated by reference.

TECHNICAL FIELD

The present disclosure relates to compounds, compositions, and methods for treating metabotropic glutamate receptor 2 related diseases and/or disorders, such as depression, anxiety, obsessive-compulsive disorder, cognitive disorders, Alzheimer's disease, and autism spectrum disorders.

BACKGROUND

Metabotropic glutamate (mGlu) receptors, a class of G-protein coupled receptor (GPCR) family C, have recently emerged as targets of potential therapeutic value. They bind glutamate, an amino acid that is the most prominent excitatory neurotransmitter in the human central nervous system (CNS). mGlus are known to activate biochemical cascades, leading to the modification of other proteins. For example, this can lead to changes in a synapse's excitability by presynaptic inhibition of neurotransmission, or modulation and even induction of postsynaptic responses.

Metabotropic glutamate receptor 2 ($mGlu_2$) is one of eight mGlus that have been identified, and, along with $mGlu_3$, is classified as a group II mGlu. Group II mGlus play an important role is synaptic plasticity, which directly effects cognitive function (including learning and memory), among other things. The effects of group II mGlus occur primarily presynaptically via their inhibition of glutamate release. These effects can also be due to the inhibition of non-vesicular glutamate release from glia. However, group II receptors are known to also reduce the activity of postsynaptic potentials, both excitatory and inhibitory, in the cortex.

Dysfunction of $mGlu_2$ has been implicated in many diseases and/or disorders. Hence, targeting $mGlu_2$ activity has been the subject of much investigation. Several reports have highlighted its link to a variety of diseases, such as depression, anxiety, obsessive-compulsive disorder, cognitive disorders, Alzheimer's disease, and autism spectrum disorders. Accordingly, there exists a need for selective modulators of $mGlu_2$.

SUMMARY

In one aspect, the invention provides compounds of formula (I), or a pharmaceutically acceptable salt thereof, (I)

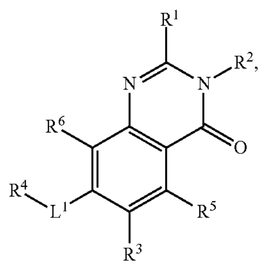

wherein:

$L^1$ is a $C_{1-6}$alkylene or $C_{1-6}$fluoroalkylene, wherein optionally 1 or 2 methylene groups in the alkylene or fluoroalkylene of $L^1$ are independently replaced with —O—, —S—, —SO—, —$SO_2$—, or —N(R)—, wherein 2 methylene groups replaced with —O—, —S—, —SO—, —$SO_2$—, or —N(R)— are separated by two or more carbon atoms in the alkylene or fluoroalkylene; and/or optionally 1 methylene group in the alkylene or fluoroalkylene of $L^1$ is replaced with -Cy-;

Cy is $C_{3-6}$cycloalkylene or a 4- to 6-membered heterocyclylene, wherein Cy is optionally substituted with 1-6 substituents independently selected from the group consisting of $C_1$-$C_4$alkyl, $C_{1-2}$fluoroalkyl, and halogen;

R, at each occurrence, is independently hydrogen or $C_{1-4}$alkyl;

$R^1$ is hydrogen or $C_{1-6}$alkyl;

$R^2$ is hydrogen or $C_{1-6}$alkyl;

$R^3$ is a 6- to 12-membered aryl or 5- to 12-membered heteroaryl, wherein $R^3$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$haloalkyl;

$R^4$ is a 6- to 12-membered aryl or 5- to 12-membered heteroaryl, wherein $R^4$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$haloalkyl; and $R^5$ and $R^6$ are each independently hydrogen, $C_{1-4}$alkyl, halogen, cyano, $C_{1-2}$haloalkyl, —$OC_{1-4}$alkyl, or —$OC_{1-2}$haloalkyl.

In another aspect, the invention provides a pharmaceutical composition comprising a compound of formula (I), or a pharmaceutically acceptable salt thereof, and a pharmaceutically acceptable carrier.

In another aspect, the invention provides a method for treating a disease or disorder associated with dysfunction of metabotropic glutamate receptor 2 ($mGlu_2$) comprising administering to a subject in need thereof, a therapeutically effective amount of the compound of formula (I), or a pharmaceutically acceptable salt or composition thereof.

In another aspect, the invention provides a method of inhibiting $mGlu_2$ activity in a subject, comprising administering to the subject a therapeutically effective amount of a compound of formula (I), or a pharmaceutically acceptable salt or composition thereof.

In another aspect, the invention provides a method of treating a disease or disorder selected from at least one of depression, anxiety, obsessive-compulsive disorder, cognitive disorders, Alzheimer's disease, and autism spectrum disorders, comprising administering to a subject in need thereof, a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of a disease or disorder selected from at least one of depression, anxiety, obsessive-compulsive disorder, cognitive disorders, Alzheimer's disease, and autism spectrum disorders.

In another aspect, the invention provides the use of a compound of formula (I), or a pharmaceutically acceptable salt or composition thereof, in the manufacture of a medicament for the treatment of a disease or disorder selected from at least one of depression, anxiety, obsessive-compulsive disorder, cognitive disorders, Alzheimer's disease, and autism spectrum disorders.

In another aspect, the invention provides a kit comprising a compound of formula (I), or a pharmaceutically acceptable salt or composition thereof, and instructions for use.

DETAILED DESCRIPTION

Disclosed herein are negative allosteric modulators (NAMs) of $mGlu_2$. The modulators can be compounds of formula (I). Compounds of formula (I) may exhibit selectivity for mGlu over other mGlu receptors. Compounds of formula (I) can be used to treat or prevent diseases and disorders associated with $mGlu_2$ by modulating $mGlu_2$ activity. $mGlu_2$ has been implicated in a number of different diseases and disorders including, but not limited to, depression, anxiety, obsessive-compulsive disorder, cognitive disorders, Alzheimer's disease, and autism spectrum disorders.

Since the orthosteric binding sites of the mGlu isoforms are highly conserved, very few selective modulators of the mGlus that bind at the orthosteric site have been identified. One strategy to selectively bind and modulate the mGlus includes identifying allosteric sites which may be amenable to modulation by a small molecule. In particular, negative allosteric modulation of $mGlu_2$ can result in inhibition of processes governed by $mGlu_2$ and provide therapeutic benefits for disorders caused by mGlu dysfunction.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

The term "alkoxy," as used herein, refers to a group —O-alkyl. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkoxyalkyl," as used herein, refers to an alkoxy group, as defined herein, appended to the parent molecular moiety through an alkyl group, as defined herein.

The term "alkoxyfluoroalkyl," as used herein, refers to an alkoxy group, as defined herein, appended to the parent molecular moiety through a fluoroalkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, $—CH_2—$, $—CD_2$-, $—CH_2CH_2—$, $—C(CH_3)(H)—$, $—C(CH_3)(D)$-, $—CH_2CH_2CH_2—$, $—CH_2CH_2CH_2CH_2—$, and $—CH_2CH_2CH_2CH_2CH_2—$.

The term "alkylamino," as used herein, means at least one alkyl group, as defined herein, is appended to the parent molecular moiety through an amino group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino," as used herein, means $—NR_xR_y$, wherein $R_x$ and $R_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be $—NR_x—$, wherein $R_x$ may be hydrogen, alkyl, cycloalkyl, aryl, heteroaryl, heterocycle, alkenyl, or heteroalkyl.

The term “aryl,” as used herein, refers to a phenyl or a phenyl appended to the parent molecular moiety and fused to a cycloalkane group (e.g., the aryl may be indan-4-yl), fused to a 6-membered arene group (i.e., the aryl is naphthyl), or fused to a non-aromatic heterocycle (e.g., the aryl may be benzo[d][1,3]dioxol-5-yl). The term “phenyl” is used when referring to a substituent and the term 6-membered arene is used when referring to a fused ring. The 6-membered arene is monocyclic (e.g., benzene or benzo). The aryl may be monocyclic (phenyl) or bicyclic (e.g., a 9- to 12-membered fused bicyclic system).

The term “cyanoalkyl,” as used herein, means at least one —CN group, is appended to the parent molecular moiety through an alkylene group, as defined herein.

The term “cyanofluoroalkyl,” as used herein, means at least one —CN group, is appended to the parent molecular moiety through a fluoroalkyl group, as defined herein.

The term “cycloalkoxy,” as used herein, refers to a cycloalkyl group, as defined herein, appended to the parent molecular moiety through an oxygen atom.

The term “cycloalkyl” or “cycloalkane,” as used herein, refers to a saturated ring system containing all carbon atoms as ring members and zero double bonds. The term “cycloalkyl” is used herein to refer to a cycloalkane when present as a substituent. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term “cycloalkenyl” or “cycloalkene,” as used herein, means a non-aromatic monocyclic or multicyclic ring system containing all carbon atoms as ring members and at least one carbon-carbon double bond and preferably having from 5-10 carbon atoms per ring. The term “cycloalkenyl” is used herein to refer to a cycloalkene when present as a substituent. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl. Exemplary monocyclic cycloalkenyl rings include cyclopentenyl, cyclohexenyl or cycloheptenyl.

The term “carbocyclyl” means a “cycloalkyl” or a “cycloalkenyl.” The term “carbocycle” means a “cycloalkane” or a “cycloalkene.” The term “carbocyclyl” refers to a “carbocycle” when present as a substituent.

The terms cycloalkylene and heterocyclylene refer to divalent groups derived from the base ring, i.e., cycloalkane, heterocycle. For purposes of illustration, examples of cycloalkylene and heterocyclylene include, respectively,

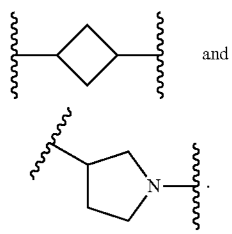

Cycloalkylene and heterocyclylene include a geminal divalent groups such as 1,1-$C_{3-6}$cycloalkylene

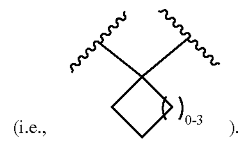

A further example is 1,1-cyclopropylene

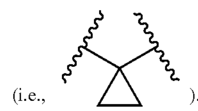 [SMILES: *C1(*)CC1]

The term “fluoroalkyl,” as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term “fluoroalkylene,” as used herein, means an alkylene group, as defined herein, in which one, two, three, four, five, six, seven or eight hydrogen atoms are replaced by fluorine. Representative examples of fluoroalkylene include, but are not limited to $—CF_2—$, $—CH_2CF_2—$, 1,2-difluoroethylene, 1,1,2,2-tetrafluoroethylene, 1,3,3,3-tetrafluoropropylene, 1,1,2,3,3-pentafluoropropylene, and perfluoropropylene such as 1,1,2,2,3,3-hexafluoropropylene.

The term “halogen” or “halo,” as used herein, means Cl, Br, I, or F.

The term “haloalkyl,” as used herein, means an alkyl group, as defined herein, in which one, two, three, four, five, six, seven or eight hydrogen atoms are replaced by a halogen.

The term “haloalkoxy,” as used herein, means at least one haloalkyl group, as defined herein, is appended to the parent molecular moiety through an oxygen atom.

The term “halocycloalkyl,” as used herein, means a cycloalkyl group, as defined herein, in which one or more hydrogen atoms are replaced by a halogen.

The term “heteroalkyl,” as used herein, means an alkyl group, as defined herein, in which one or more of the carbon atoms has been replaced by a heteroatom selected from the group consisting of S, O, P and N. Representative examples of heteroalkyls include, but are not limited to, alkyl ethers, secondary and tertiary alkyl amines, amides, and alkyl sulfides.

The term “heteroaryl,” as used herein, refers to an aromatic monocyclic heteroatom-containing ring (monocyclic heteroaryl) or a bicyclic ring system containing at least one monocyclic heteroaromatic ring (bicyclic heteroaryl). The term “heteroaryl” is used herein to refer to a heteroarene when present as a substituent. The monocyclic heteroaryl are five or six membered rings containing at least one heteroatom independently selected from the group consisting of N, O and S (e.g. 1, 2, 3, or 4 heteroatoms independently selected from the group consisting of O, S, and N). The five membered aromatic monocyclic rings have two double bonds and the six membered aromatic monocyclic rings have three double bonds. The bicyclic heteroaryl is an 8- to 12-membered ring system and includes a fused bicyclic heteroaromatic ring system (i.e., 10π electron system) such as a monocyclic heteroaryl ring fused to a 6-membered arene (e.g., quinolin-4-yl, indol-1-yl), a monocyclic heteroaryl ring fused to a monocyclic heteroarene (e.g., naphthyridinyl), and a phenyl fused to a monocyclic heteroarene (e.g., quinolin-5-yl, indol-4-yl). A bicyclic heteroaryl/heteroarene group includes a 9-membered fused bicyclic heteroaromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. A bicyclic heteroaryl also includes a fused bicyclic ring system composed of one heteroaromatic ring and one non-aromatic ring such as a monocyclic heteroaryl ring fused to a monocyclic carbocyclic ring (e.g., 6,7-dihydro-5H-cyclopenta[b]pyridinyl), or a monocyclic heteroaryl ring fused to a monocyclic heterocycle (e.g., 2,3-dihydrofuro[3,2-b]pyridinyl). The bicyclic heteroaryl is attached to the parent molecular moiety at an aromatic ring atom. Other representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The term "heterocyclyl" is used herein to refer to a heterocycle when present as a substituent. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocyclyls include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a 6-membered arene, or a monocyclic heterocycle fused to a monocyclic cycloalkane, or a monocyclic heterocycle fused to a monocyclic cycloalkene, or a monocyclic heterocycle fused to a monocyclic heterocycle, or a monocyclic heterocycle fused to a monocyclic heteroarene, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocyclyl is attached to the parent molecular moiety at a non-aromatic ring atom (e.g., indolin-1-yl). Representative examples of bicyclic heterocyclyls include, but are not limited to, chroman-4-yl, 2,3-dihydrobenzofuran-2-yl, 2,3-dihydrobenzothien-2-yl, 1,2,3,4-tetrahydroisoquinolin-2-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indol-1-yl, isoindolin-2-yl, octahydrocyclopenta[c]pyrrolyl, octahydropyrrolopyridinyl, tetrahydroisoquinolinyl, 7-oxabicyclo[2.2.1]heptanyl, hexahydro-2H-cyclopenta[b]furanyl, 2-oxaspiro[3.3]heptanyl, 3-oxaspiro[5.5]undecanyl, 6-oxaspiro[2.5]octan-1-yl, and 3-oxabicyclo[3.1.0]hexan-6-yl. Tricyclic heterocycles are exemplified by a bicyclic heterocycle fused to a 6-membered arene, or a bicyclic heterocycle fused to a monocyclic cycloalkane, or a bicyclic heterocycle fused to a monocyclic cycloalkene, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocyclyls are connected to the parent molecular moiety at a non-aromatic ring atom.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

Terms such as "alkyl," "cycloalkyl," "alkylene," etc. may be preceded by a designation indicating the number of atoms present in the group in a particular instance (e.g., "$C_{1-4}$ alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

2. Compounds

A. Compounds of Formula (I)

In one aspect, the invention provides compounds of formula (I), wherein $L^1$, $R^1$, $R^2$, $R^3$, $R^4$, $R^5$, and $R^6$ are as defined herein. As described below, formula (I) may have subformula (Ia) or (Ib).

Unsubstituted or substituted rings (i.e., optionally substituted) such as aryl, heteroaryl, etc. are composed of both a ring system and the ring system's optional substituents. Accordingly, the ring system may be defined independently of its substituents, such that redefining only the ring system leaves any previous optional substituents present. For example, a 5- to 12-membered heteroaryl with optional substituents may be further defined by specifying the ring system of the 5- to 12-membered heteroaryl is a 5- to 6-membered heteroaryl (i.e., 5- to 6-membered heteroaryl ring system), in which case the optional substituents of the 5- to 12-membered heteroaryl are still present on the 5- to 6-membered heteroaryl, unless otherwise expressly indicated.

In the following, embodiments of the invention are disclosed. The first embodiment is denoted E1, the next embodiments are denoted E1.1, E1.2, E1.3, E2 and so forth.

E1. A compound of formula (I), or a pharmaceutically acceptable salt thereof, (I)

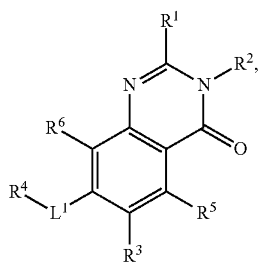

wherein:

$L^1$ is a $C_{1-6}$alkylene or $C_{1-6}$fluoroalkylene, wherein optionally 1 or 2 methylene groups in the alkylene or fluoroalkylene of $L^1$ are independently replaced with —O—, —S—, —SO—, —$SO_2$—, or —N(R)—, wherein 2 methylene groups replaced with —O—, —S—, —SO—, —$SO_2$—, or —N(R)— are separated by two or more carbon atoms in the alkylene or fluoroalkylene; and/or optionally 1 methylene group in the alkylene or fluoroalkylene of $L^1$ is replaced with -Cy-;

Cy is $C_{3-6}$cycloalkylene or a 4- to 6-membered heterocyclylene, wherein Cy is optionally substituted with 1-6 substituents independently selected from the group consisting of $C_1$-$C_4$alkyl, $C_{1-2}$fluoroalkyl, and halogen;

R, at each occurrence, is independently hydrogen or $C_{1-4}$alkyl;

$R^1$ is hydrogen or $C_{1-6}$alkyl;

$R^2$ is hydrogen or $C_{1-6}$alkyl;

$R^3$ is a 6- to 12-membered aryl or 5- to 12-membered heteroaryl, wherein $R^3$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$haloalkyl;

$R^4$ is a 6- to 12-membered aryl or 5- to 12-membered heteroaryl, wherein $R^4$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$haloalkyl; and $R^5$ and $R^6$ are each independently hydrogen, $C_{1-4}$alkyl, halogen, cyano, $C_{1-2}$haloalkyl, —$OC_{1-4}$alkyl, or —$OC_{1-2}$haloalkyl.

E1.1. The compound of E1, or a pharmaceutically acceptable salt thereof, wherein $L^1$ is a $C_{1-6}$alkylene or $C_{1-6}$fluoroalkylene, wherein optionally 1 or 2 methylene groups in the alkylene or fluoroalkylene of $L^1$ are independently replaced with —O—, —S—, —SO—, —$SO_2$—, or —N(R)—, wherein 2 methylene groups replaced with —O—, —S—, —SO—, —$SO_2$—, or —N(R)— are separated by two or more carbon atoms in the alkylene or fluoroalkylene.

E1.2 The compound of E1.1, or a pharmaceutically acceptable salt thereof, wherein $L^1$ is

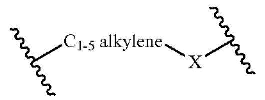

wherein X is selected from the group consisting of —O—, —S—, —SO—, —$SO_2$—, and —N(R)—.

E1.3. The compound of E1.2, or a pharmaceutically acceptable salt thereof, wherein $R^4$-$L^1$ is

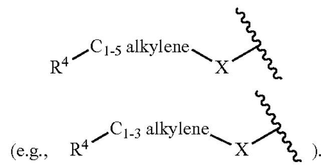

E2. The compound of E1 or E1.1, or a pharmaceutically acceptable salt thereof, wherein $L^1$ is a $C_{1-4}$alkylene, wherein 1 or 2 methylene groups in the alkylene of $L^1$ are replaced with —O—, wherein 2 methylene groups replaced with —O— are separated by two or more carbon atoms in the alkylene.

E3. The compound of any one of E1, E1.1, or E2, or a pharmaceutically acceptable salt thereof, wherein $L^1$ is a $C_{2-3}$alkylene, wherein 1 methylene group in the alkylene of $L^1$ is replaced with —O—.

E3.1. The compound of E2 or E3, or a pharmaceutically acceptable salt thereof, wherein $L^1$ attaches to the parent molecular moiety through an oxygen atom in $L^1$.

E3.2. The compound of E3 or E3.1, or a pharmaceutically acceptable salt thereof, wherein $L^1$ is

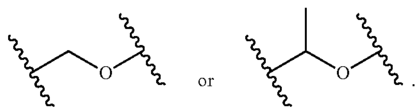

E3.3. The compound of any of E3-E3.2, or a pharmaceutically acceptable salt thereof, wherein

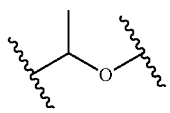 [SMILES: *OC(*)C]

at $L^1$ is

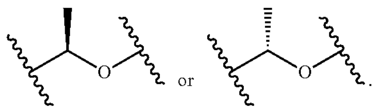

E4. The compound of any one of E1-E3.2, or a pharmaceutically acceptable salt thereof, wherein $L^1$ is

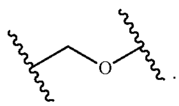 [SMILES: *CO*]

E4.1. The compound of any one of E1-E4, or a pharmaceutically acceptable salt thereof, wherein

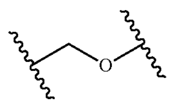 [SMILES: *CO*]

at $L^1$ is

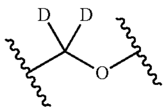

E4.2. The compound of any one of E1-E4.1, or a pharmaceutically acceptable salt thereof, wherein $R^4$-$L^1$- is

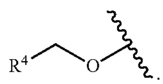

E5. The compound of any one of E1-E4, or a pharmaceutically acceptable salt thereof, wherein $R^2$ is hydrogen.

E6. The compound of any one of E1-E5, or a pharmaceutically acceptable salt thereof, wherein $R^4$ is the unsubstituted or substituted 5- to 12-membered heteroaryl.

E7. The compound of any one of E1-E6, or a pharmaceutically acceptable salt thereof, wherein the ring system of the unsubstituted or substituted 5- to 12-membered heteroaryl at $R^4$ is an 8- to 10-membered fused bicyclic heteroaryl having 2-4 double bonds and 1-4 heteroatoms independently selected from the group consisting of N, O, and S.

E8. The compound of any one of E1-E7, or a pharmaceutically acceptable salt thereof, wherein $R^4$ is an unsubstituted 9-membered fused bicyclic heteroaryl having 2 double bonds and 1-3 heteroatoms independently selected from the group consisting of N and O.

E9. The compound of any one of E1-E8 or a pharmaceutically acceptable salt thereof, wherein $R^4$ is

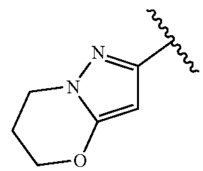

E10. The compound of any one of E1-E6, or a pharmaceutically acceptable salt thereof, wherein the ring system of the unsubstituted or substituted 5- to 12-membered heteroaryl at $R^4$ is a 5- or 6-membered monocyclic heteroaryl having 1 or 2 heteroatoms independently selected from the group consisting of N, O, and S.

E11. The compound of E10, or a pharmaceutically acceptable salt thereof, wherein the ring system of the unsubstituted or substituted 5- or 6-membered monocyclic heteroaryl is pyridinyl, imidazolyl, thiazolyl, pyrazolyl, or oxazolyl.

E11.1. The compound of E11, or a pharmaceutically acceptable salt thereof, wherein the ring system of the unsubstituted or substituted 5- or 6-membered monocyclic heteroaryl is pyrazolyl.

E11.2. The compound of E10, E11, or E11.1, or a pharmaceutically acceptable salt thereof, wherein the 5- or 6-membered monocyclic heteroaryl is unsubstituted or substituted with 1 substituent selected from the group consisting of $C_{1-4}$alkyl and $C_{1-2}$haloalkyl.

E11.3. The compound of E11.2, or a pharmaceutically acceptable salt thereof, wherein the 5- or 6-membered monocyclic heteroaryl is substituted with 1 $C_{1-4}$alkyl substituent.

E12. The compound of E11, or a pharmaceutically acceptable salt thereof, wherein $R^4$ is

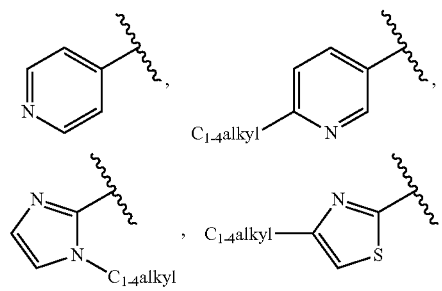

-continued

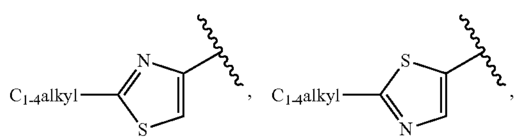

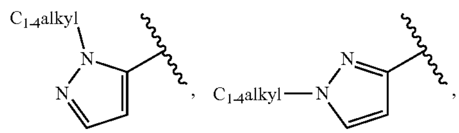

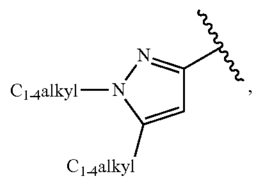

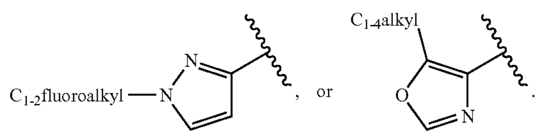

E12.1 The compound of E12, or a pharmaceutically acceptable salt thereof wherein $R^4$ is

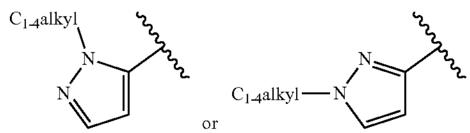

E12.2 The compound of E11, or a pharmaceutically acceptable salt thereof, wherein $R^4$ is

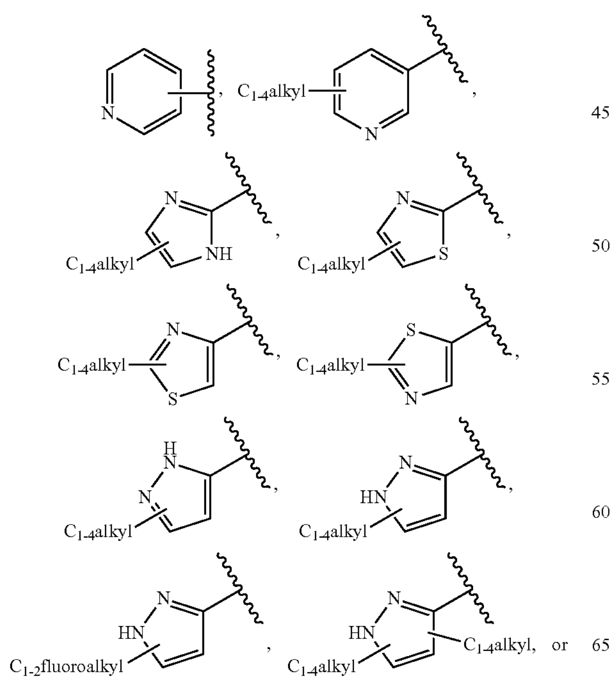

-continued

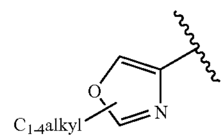

E12.3 The compound of E12.2, or a pharmaceutically acceptable salt thereof, wherein $R^4$ is

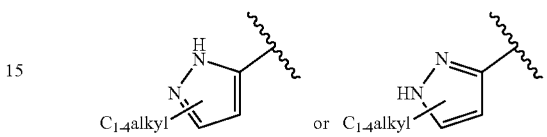

E12.4. The compound of E12.2, or a pharmaceutically acceptable salt thereof, wherein $R^4$ is

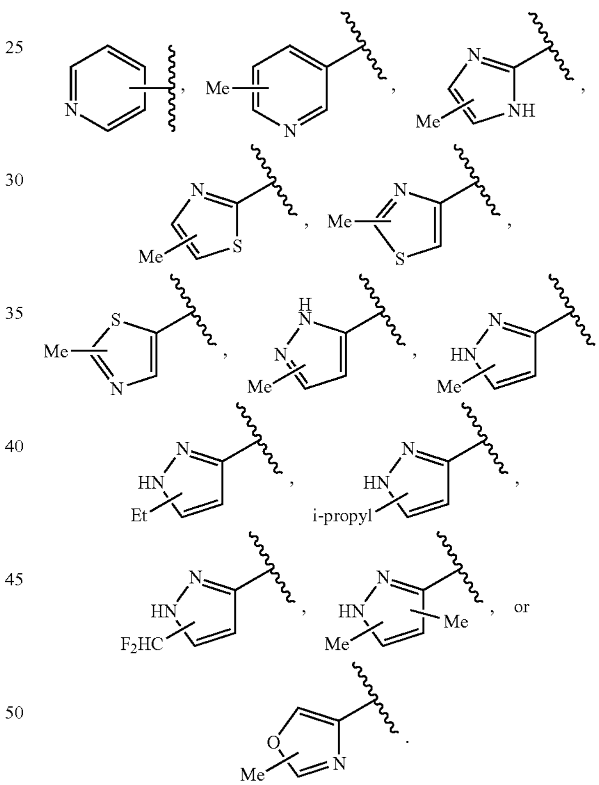

E12.5. The compound of E12.4, or a pharmaceutically acceptable salt thereof, wherein $R^4$ is

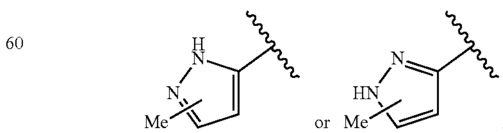

E13. The compound of E12, or a pharmaceutically acceptable salt thereof, wherein $R^4$ is

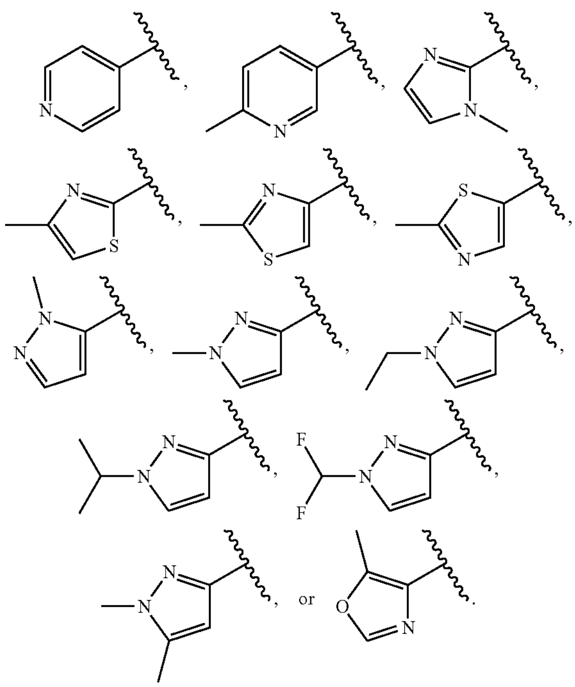

E13.1 The compound of E13, or a pharmaceutically acceptable salt thereof, wherein $R^4$ is

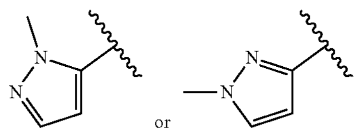

E14. The compound of any one of E1-E5, or a pharmaceutically acceptable salt thereof, wherein $R^4$ is the unsubstituted or substituted 6- to 12-membered aryl.

E14.1. The compound of any one of E1-E5 or E14, or a pharmaceutically acceptable salt thereof, wherein the ring system of the unsubstituted or substituted 6- to 12-membered aryl at $R^4$ is phenyl.

E14.2. The compound of E14.1, or a pharmaceutically acceptable salt thereof, wherein $R^4$ is

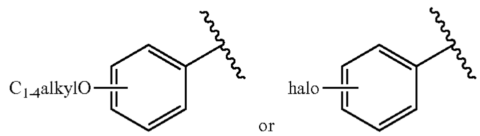

E14.3. The compound of E14.2, or a pharmaceutically acceptable salt thereof, wherein $R^4$ is

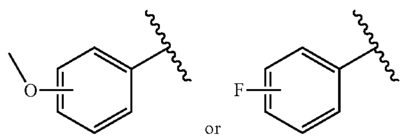

E14.4. The compound of E14.2, or a pharmaceutically acceptable salt thereof, wherein $R^4$ is

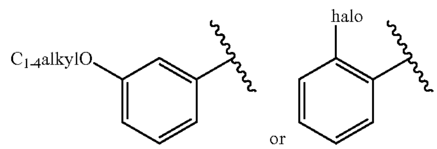

E14.5. The compound of E14.4, or a pharmaceutically acceptable salt thereof, wherein $R^4$ is

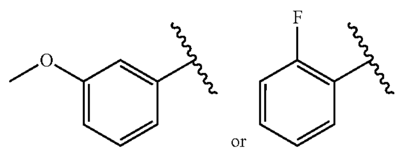

E15. The compound of any one of E1-E14.5, or a pharmaceutically acceptable salt thereof, wherein $R^3$ is the unsubstituted or substituted 6- to 12-membered aryl.

E16. The compound of any one of E1-E15, or a pharmaceutically acceptable salt thereof, wherein the ring system of the unsubstituted or substituted 6- to 12-membered aryl at $R^3$ is phenyl.

E17. The compound of E16, or a pharmaceutically acceptable salt thereof, wherein $R^3$ is

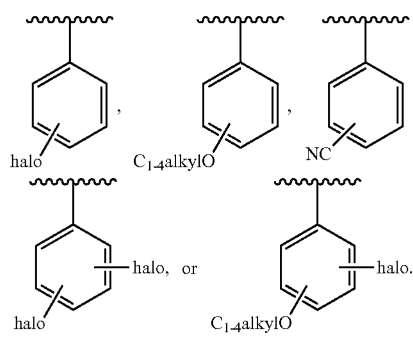

E17.1 The compound of E17, or a pharmaceutically acceptable salt thereof, wherein $R^3$ is

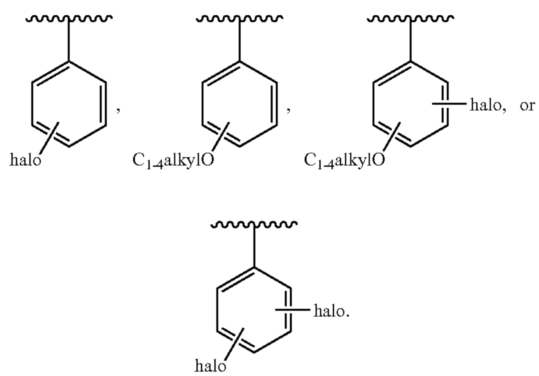

E17.2. The compound of E17, or a pharmaceutically acceptable salt thereof, wherein $R^3$ is

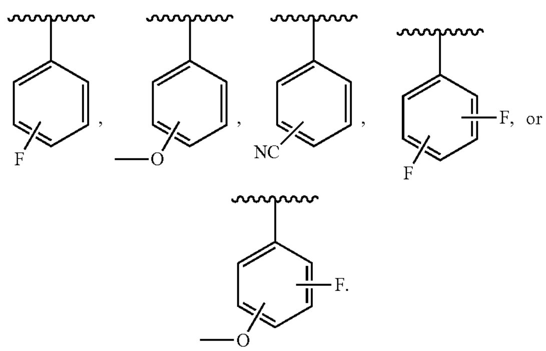

E17.3 The compound of E17.2, or a pharmaceutically acceptable salt thereof, wherein $R^3$ is

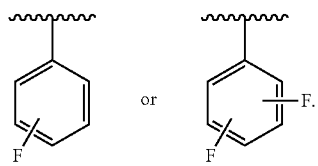

E17.4. The compound of E17.2, or a pharmaceutically acceptable salt thereof, wherein $R^3$ is

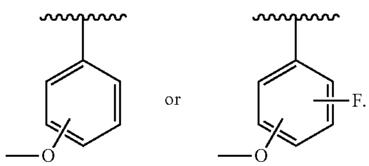

E17.5. The compound of E17.4, or a pharmaceutically acceptable salt thereof, wherein

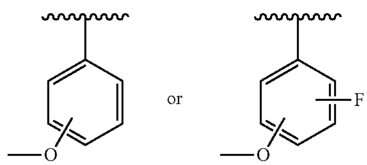

at $R^3$ is, respectively,

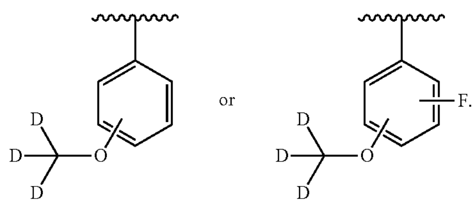

E18. The compound of E17, or a pharmaceutically acceptable salt thereof, wherein $R^3$ is

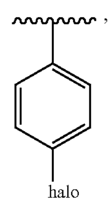

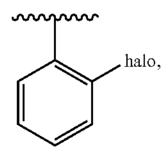

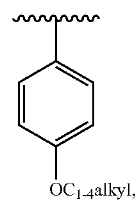

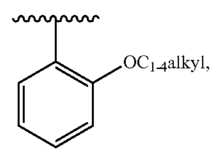

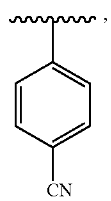

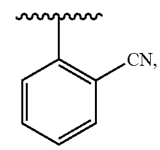

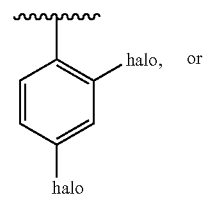

or

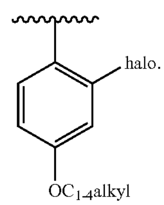

E18.1 The compound of E18, or a pharmaceutically acceptable salt thereof, wherein $R^3$ is

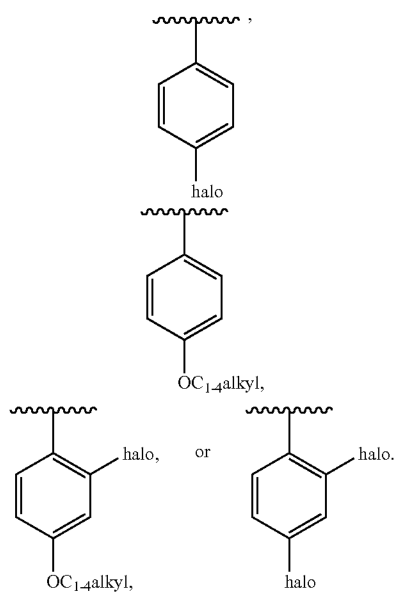

E19. The compound of E18, or a pharmaceutically acceptable salt thereof, wherein $R^3$ is

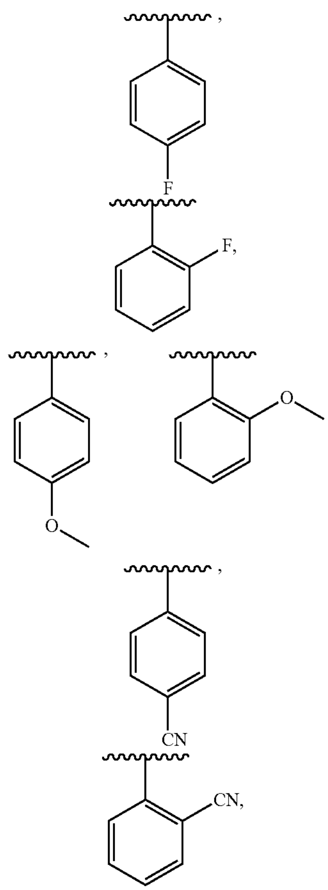

-continued

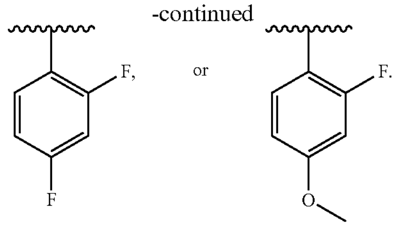

E19.1. The compound of E19, or a pharmaceutically acceptable salt thereof, wherein $R^3$ is

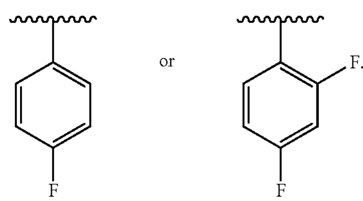 [SMILES: *c1ccc(F)cc1 ; "or" ; *c1ccc(F)cc1F]

E19.2. The compound of E19, or a pharmaceutically acceptable salt thereof, wherein $R^3$ is

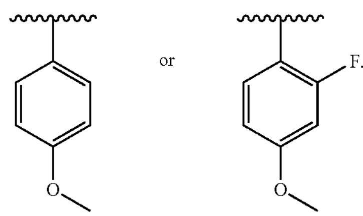

E19.3. The compound of E19.2, or a pharmaceutically acceptable salt thereof, wherein the

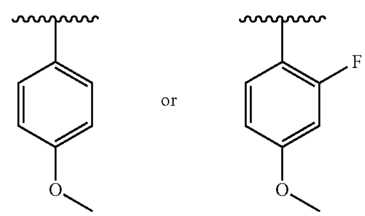

at $R^3$ is, respectively,

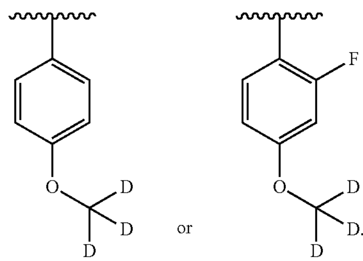

E20. The compound of any one of E1-E14.5, or a pharmaceutically acceptable salt thereof, wherein $R^3$ is the unsubstituted or substituted 5- to 12-membered heteroaryl.

E21. The compound of E20, or a pharmaceutically acceptable salt thereof, wherein the ring system of the unsubstituted or substituted 5- to 12-membered heteroaryl at $R^3$ is a 5- or 6-membered monocyclic heteroaryl having 1 or 2 heteroatoms independently selected from the group consisting of N, O, and S.

E22. The compound of E21, or a pharmaceutically acceptable salt thereof, wherein the ring system of the unsubstituted or substituted 5- or 6-membered monocyclic heteroaryl is pyrrolyl.

E23. The compound of E22, or a pharmaceutically acceptable salt thereof, wherein $R^3$ is

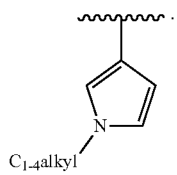

E24. The compound of E23, or a pharmaceutically acceptable salt thereof, wherein $R^3$ is

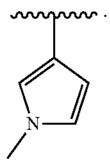

E25. The compound of any one of E1-E24, or a pharmaceutically acceptable salt thereof, wherein $R^5$ and $R^6$ are each independently selected from the group consisting of hydrogen, $C_{1-4}$alkyl, and halogen.

E26. The compound of any one of E1-E25, or a pharmaceutically acceptable salt thereof, wherein $R^5$ and $R^6$ are each hydrogen.

E27. The compound of any one of E1-E26, or a pharmaceutically acceptable salt thereof, wherein $R^1$ is hydrogen.

E28. The compound of any one of E1-E27, or a pharmaceutically acceptable salt thereof, wherein the compound is a compound of formula (Ia):

(Ia)

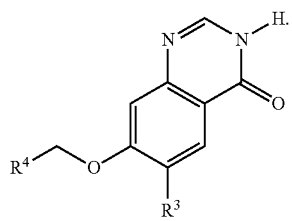

E28.1. The compound of E28, or a pharmaceutically acceptable salt thereof, wherein the compound of formula (Ia) is

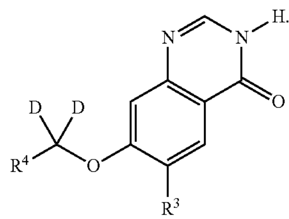

E29. The compound of E1, selected from the group consisting of:

6-(4-fluorophenyl)-7-((1-methyl-1H-pyrazol-3-yl)methoxy)quinazolin-4(3H)-one;

6-(4-fluorophenyl)-7-((1-methyl-1H-pyrazol-5-yl)methoxy)quinazolin-4(3H)-one;

7-((6,7-dihydro-4H-pyrazolo[5,1-c][1,4]oxazin-2-yl)methoxy)-6-(4-fluorophenyl)quinazolin-4(3H)-one;

6-(2-fluoro-4-methoxyphenyl)-7-((1-methyl-1H-pyrazol-3-yl)methoxy)quinazolin-4(3H)-one;

6-(2,4-difluorophenyl)-7-((1-methyl-1H-pyrazol-3-yl)methoxy)quinazolin-4(3H)-one;

7-((1-methyl-1H-pyrazol-3-yl)methoxy)-6-(1-methyl-1H-pyrrol-3-yl)quinazolin-4(3H)-one;

6-(4-methoxyphenyl)-7-((1-methyl-1H-pyrazol-3-yl)methoxy)quinazolin-4(3H)-one; and 7-((6,7-dihydro-4H-pyrazolo[5,1-c][1,4]oxazin-2-yl)methoxy)-6-(4-methoxyphenyl)quinazolin-4(3H)-one;

or a pharmaceutically acceptable salt thereof.

E30. A pharmaceutical composition comprising the compound of any one of E1-E29, or a pharmaceutically acceptable salt thereof, and a pharmaceutically acceptable carrier.

E31. A method for treating a disease or disorder associated with dysfunction of metabotropic glutamate receptor 2 ($mGlu_2$) comprising administering to a subject in need thereof, a therapeutically effective amount of the compound of any one of E1-E29, or a pharmaceutically acceptable salt thereof, or the pharmaceutical composition of E30.

E32. The method of E31, wherein the disease or disorder is selected from at least one of depression, anxiety, obsessive-compulsive disorder, cognitive disorders, Alzheimer's disease, and autism spectrum disorders.

E33. A compound of any one of E1-E29, or a pharmaceutically acceptable salt thereof, or the pharmaceutical composition of E30, for use in the treatment of a disease or disorder selected from at least one of depression, anxiety, obsessive-compulsive disorder, cognitive disorders, Alzheimer's disease, and autism spectrum disorders.

E34. Use of a compound of any one of E1-E29, or a pharmaceutically acceptable salt thereof, or the pharmaceutical composition of E30, in the manufacture of a medicament for the treatment of a disease or disorder selected from at least one of depression, anxiety, obsessive-compulsive disorder, cognitive disorders, Alzheimer's disease, and autism spectrum disorders.

Compound names can be assigned by using Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

In the compounds of formula (I), and any subformulas, any "hydrogen" or "H," whether explicitly recited or implicit in the structure, encompasses hydrogen isotopes $^1H$ (protium) and $^2H$ (deuterium).

The present disclosure also includes isotopically-labeled compounds (e.g., deuterium labeled), where an atom in the isotopically-labeled compound is specified as a particular isotope of the atom. Examples of isotopes suitable for inclusion in the compounds of the invention are hydrogen, carbon, nitrogen, oxygen, phosphorus, sulfur, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Isotopically-enriched forms of compounds of formula (I), or any subformulas, may generally be prepared by conventional techniques known to those skilled in the art or by processes analogous to those described in the accompanying Examples using an appropriate isotopically-enriched reagent in place of a non-isotopically-enriched reagent. The extent of isotopic enrichment can be characterized as a percent incorporation of a particular isotope at an isotopically-labeled atom (e.g., % deuterium incorporation at a deuterium label).

B. Allosteric Modulation of $mGlu_2$

The disclosed compounds may act or function as non-competitive antagonists, allosteric inhibitors, allosteric antagonists, or negative allosteric modulators (NAM) of $mGlu_2$. The compounds may be procognitive and neuroprotective even in the presence of $mGlu_2$ dysfunction.

Compounds of formula (I) can inhibit $mGlu_2$ with an $IC_{50}$ ranging from about 1 nM to about 30 μM. The compounds may have an $IC_{50}$ of about 30 μM, about 29 μM, about 28 μM, about 27 μM, about 26 μM, about 25 μM, about 24 μM, about 23 μM, about 22 μM, about 21 μM, about 20 μM, about 19 μM, about 18 μM, about 17 μM, about 16 μM, about 15 μM, about 14 μM, about 13 μM, about 12 μM, about 11 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of formula (I) can inhibit $mGlu_2$ with an IC50 of less than 30 μM, less than 29 μM, less than 28 μM, less than 27 μM, less than 26 μM, less than 25 μM, less than 24 μM, less than 23 μM, less than 22 μM, less than 21 μM, less than 20 μM, less than 19 μM, less than 18 μM, less than 17 μM, less than 16 μM, less than 15 μM, less than 14 μM, less than 13 μM, less than 12 μM, less than 11 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

Compounds of formula (I) may be selective modulators of $mGlu_2$ over $mGlu_3$. The compounds may have a ratio of $mGlu_2$ $IC_{50}$ to $mGlu_3$ $EC_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of $mGlu_2$ $IC_{50}$ to $mGlu_3$ $EC_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

Compounds of formula (I) may be selective modulators of $mGlu_2$ over $mGlu_5$. The compounds may have a ratio of $mGlu_2$ $IC_{50}$ to $mGlu_5$ $EC_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of $mGlu_2$ $IC_{50}$ to $mGlu_5$ $EC_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

C. Pharmaceutical Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

D. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations which have been used in the descriptions of the Schemes that follow are:

$Pd(dppf)Cl_2$ is [1,1'-Bis(diphenylphosphino)ferrocene]dichloropalladium(II).

Compounds of formula (I) or any of its subformulas may be synthesized as shown in the following schemes.

General Scheme 1

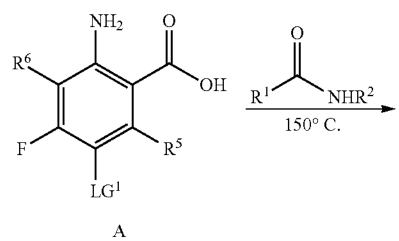

A

-continued

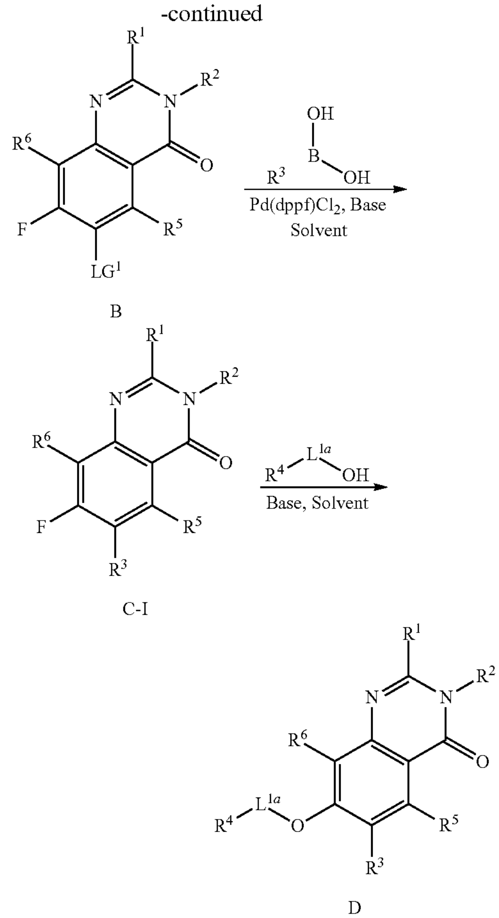

B

C-I

D

As shown in General Scheme 1, 2-amino benzoic acid compounds of formula A, where $LG^1$ is halogen, tosylate, or mesylate, may be subjected to cyclization conditions, wherein compound A is reacted with an appropriate $R^2$-substituted amide at elevated temperature (e.g., 150° C.) to form the intermediate compound of formula B. The intermediate compound B may be subjected to Suzuki reaction conditions, wherein compound B is reacted with an appropriate $R^3$-substituted boronic acid or ester to form intermediate compound of formula C-I. Finally, the intermediate compound C-I may be subjected to Nucleophilic Aromatic Substitution (SNAr) conditions, wherein compound C-I is reacted with an appropriate $R^4$-$L^1$-OH reagent in the presence of a base (e.g. NaH) to provide the quinazolin-4(3H)-one compound of formula D.

General Scheme 2

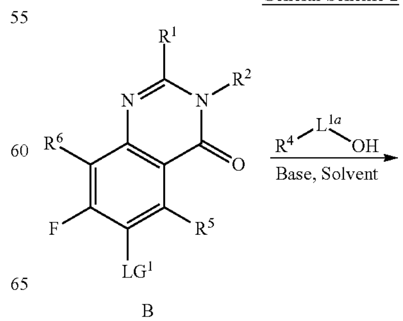

B

-continued

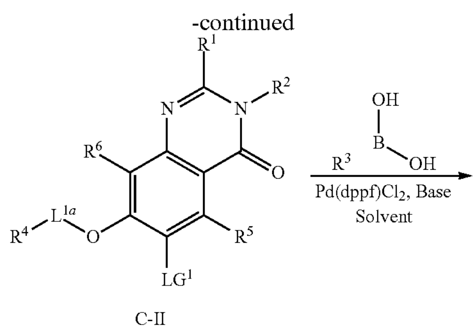

C-II

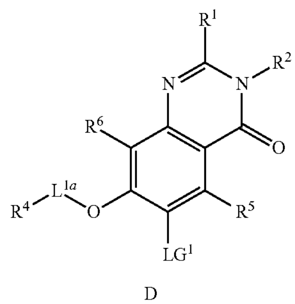

D

As shown in General Scheme 2, quinazolinone compounds of formula B may be subjected to Nucleophilic Aromatic Substitution (SNAr) conditions, wherein compound B is reacted with an appropriate $R^4$-$L^1$-OH reagent in the presence of a base (e.g., NaH) to provide intermediate compound C-II. Intermediate C-II may be subjected to Suzuki reaction conditions, wherein compound C-II is reacted with an appropriate $R^3$-substituted boronic acid or ester to form the quinazolin-4(3H)-one compound of formula D.

In General Schemes 1 and 2, "-$L^{1a}$-O—" corresponds to $L^1$ bonded to the parent molecular moiety through an oxygen atom in $L^1$.

Suzuki coupling conditions suitable for use in the processes of General Schemes 1 and 2 are well known in the art. Suitable Suzuki conditions include those generally outlined in General Schemes 1 and 2, as described in the Examples herein.

Boronic acid and ester reagents

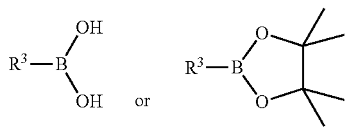

may be prepared from the corresponding halide (e.g., bromide) using known procedures.

Nucleophilic Aromatic Substitution (SNAr) conditions suitable for use in the processes of General Schemes 1 and 2 are well known in the art. Suitable SNAr conditions include those generally outlined in General Schemes 1 and 2, and as described in the Examples herein.

Cyclization conditions suitable for use in the processes of General Scheme 1 are well known in the art. Suitable cyclization conditions include those generally outlined in General Scheme 1, and as described in the Examples herein.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered, and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

The disclosed compounds and compositions may be used in methods for treatment of $mGlu_2$ related medical disorders and/or diseases. The methods of treatment may comprise administering to a subject in need of such treatment a composition comprising a therapeutically effective amount of the compound of formula (I).

The compositions can be administered to a subject in need thereof to modulate $mGlu_2$, for a variety of diverse biological processes. The present disclosure is directed to methods for administering the composition to inhibit $mGlu_2$, a GPCR that plays a role in synaptic plasticity, which directly effects cognitive function and memory, for example.

The compositions may be useful for treating and preventing certain diseases and disorders in humans and animals related to $mGlu_2$ dysfunction. Treatment or prevention of such diseases and disorders can be effected by modulating $mGlu_2$ in a subject, by administering a compound or composition of the invention, either alone or in combination with another active agent as part of a therapeutic regimen to a subject in need thereof.

A. Depression

Antidepressant-like effects of the $mGlu_{2/3}$ receptor antagonists, MGS0039 and LY341495, were first demonstrated in the rat forced swim test (FST) and mouse tail-suspension test (TST) using normal animals (Chaki et al. *Neuropharmacology,* 2004, 46, 457-467). More recently, studies have attempted to evaluate the effects of these drugs in paradigms implicated in the etiology of human depression. MGS0039 exhibited antidepressant effects in the learned helplessness test where treatment with MGS0039 for 7 days significantly reduced the number of escape failures (Yoshimizu et al. *Psychopharmacology,* 2006, 186, 587-593).

Palucha-Poniewiera et al. *Psychopharmacology,* 2010, 212, 523-535 evaluated a potential antidepressant-like effect of MGS0039 in the olfactory bulbectomy (OB) model of depression in rats. A surgical lesion of the olfactory bulbs in animals is known to induce significant behavioral, physiological, endocrine and immune changes, many of which are qualitatively similar to those observed in depressive patients. Repeated administration of MGS0039 for 14 days attenuated the hyperactivity of olfactory bulbectomized rats in the open field test and attenuated the learning deficit in the passive avoidance test.

Kawasaki et al. *Neuropharmacology,* 2011, 60, 397-404 also examined the effect of MGS0039 on behaviors of social isolation-reared mice in the FST. Rearing rodents in isolation after weaning is known to lead to changes in brain neurochemistry that produce perturbations in behavior. Post-weaning chronic social isolation for more than 6 weeks increased immobility in the FST, suggesting that isolation rearing caused depression-like behavior. MGS0039 reversed the increased immobility of social isolation reared mice in the test.

Campo, B. et al. *J. Neurogenetics* 2011, 25, 152-166, demonstrated a selective group II ($mGlu_2$ and $mGlu_3$) negative allosteric modulator (RO4491533) to be effective in several in vitro biochemical assays and in vivo models of depression. RO4491533 was shown to engage the central $mGlu_2$ and $mGlu_3$ receptors as the compound reversed the hypolocomotor effect of an $mGlu_{2/3}$ agonist (LY379268) in a target-specific manner. The known group II $mGlu_{2/3}$ antagonist LY341495 achieved the same result. RO4491533 and LY341495 dose-dependently reduced immobility time of C57Bl6/J mice in the FST. RO4491533 and LY341495 were also active in the tail suspension test in a line of Helpless (H) mice, a putative genetic model of depression.

Blockade of $mGlu_{2/3}$ receptors and ketamine may converge to the same neuronal circuits, which include activation of AMPA receptor and mTOR signaling. Because both AMPA receptor stimulation and subsequent mTOR signaling activation are presumed to be involved in rapid action of ketamine for patients with treatment-resistant depression (TRD), $mGlu_{2/3}$ receptor antagonists could exert the same effects in humans. This assumption is underpinned by several animal studies. First, the $mGlu_{2/3}$ receptor antagonist MGS0039 exhibited antidepressant effects in an animal model (the learned helplessness paradigm) which is refractory to currently prescribed antidepressants (Yoshimizu et al. *Psychopharmacology,* 2006, 186, 587-593). Second, although evidence of rapid onset of action with $mGlu_{2/3}$ receptor antagonists are absent, an AMPA receptor potentiator (AMPA receptor potentiation mediates antidepressant effects of $mGlu_{2/3}$ receptor antagonists) showed faster effects (during the first week of treatment) compared to fluoxetine (after two weeks) in a dominant-submissive test (Knapp et al. *Eur. J. Pharmacol.* 2002, 440, 121-125). Moreover, LY341495 exhibited a potent antidepressant effect in helpless mice following acute administration, while fluoxetine exerts a full antidepressant effect following chronic (21 days) treatment (Campo, B. et al. *J. Neurogenetics* 2011, 25, 152-166; E1 Yacoubi et al. *PNAS,* 2003, 100, 6227-6232). Therefore, blockade of $mGlu_{2/3}$ receptors may show rapid and potent antidepressant effects in humans.

B. Cognitive Disorders

Woltering et al. *Bioorg. Med. Chem. Lett.* 2010, 20, 6969-74, demonstrated that a negative allosteric modulator of $mGlu_{2/3}$ reversed $mGlu_{2/3}$ agonist or scopolamine-induced working memory deficits in the delayed match to position (DMTP) task in rodents, a measure of working memory. Additionally, Woltering demonstrated a synergistic reversal of scopolamine-induced deficits in DMTP when low doses of a negative allosteric modulator of $mGlu_{2/3}$ were combined with a threshold dose of the acetylcholinesterase inhibitor donezepil. Given the efficacy of donepezil and other acetylcholinesterase inhibitors in the treatment of the cognitive impairments in Alzheimer's disease, negative allosteric modulators of $mGlu_2$ may have efficacy as cognitive enhancers.

C. Obsessive-Compulsive Disorder

Shimazaki, T. et al. *Eur. J. Pharmacol.* 2004, 501, 121-125, demonstrated that MGS0039 induced glutamatergic change in mice, resulting in anti-obsessive-compulsive disorder activity. In these studies, a marble-burying behavioral test was utilized as a model for obsessive-compulsive disorder. The marble-burying behavior test is recognized as a useful model for evaluating the clinical potential of anti-obsessive-compulsive disorder drugs. Specifically, MGS0039 treated mice exhibited reduced marble-burying behavior in a significant and dose dependent manner, while no significant change was observed in spontaneous locomotor activity. In addition, LY341495, another potent antagonist of group II mGlu receptors, was also shown to significantly reduce marble-burying behavior in treated mice.

D. Alzheimer's Disease

Kim, S. H. et al. *Molecular Psychiatry* 2014, 1-8, have assessed the therapeutic potential of chronic pharmacological inhibition of group II mGlu receptors ($mGlu_2$ and $mGlu_3$) with a group II mGlu receptor antagonist in an APP transgenic mouse model that develops impaired learning behavior in relation to accumulation of mutant Aβ oligomers that never form amyloid plaques. Once-daily dosing of the orally bioavailable prodrug, BCI-838, delivered a sufficient brain concentration of its active metabolite BCI-632 to inhibit group II mGlu receptors for 22 hours. Three months of treatment with BCI-838 provided anxiolytic effects, reversed Dutch APP transgene-associated learning and memory impairment, and decreased the levels of monomeric and oAβ peptides in the hippocampus and cortex of the two different AD mouse models. Notably, BCI-838 administration stimulated hippocampal progenitor cell proliferation in both wild-type and Alzheimer's diseased mice for 3 months, which resulted in significantly increased numbers of newborn neurons in the hippocampi of Dutch APP transgenic mice. In addition to treatment, the proneurogenic properties make the compound attractive for potential use in reversing some of the early symptoms of Alzheimer's disease (AD), possibly through reparative effects of the newborn neurons. These findings suggest that chronic pharmacological inhibition of group II mGlu receptors has the potential to be a disease-modifying treatment for AD that targets cognitive/emotional defects and modulates neurogenesis.

Additional studies by Caraci, F. et al *Mol. Pharmacol.* 2011, 79, 618-626, showed that a positive allosteric modulator of $mGlu_2$ (LY566332) amplified Aβ-induced neurodegeneration, but this effect was prevented by the $mGlu_{2/3}$ receptor antagonist, LY341495.

E. Anxiety

Yoshimizu et al. *Psychopharmacology,* 2006, 186, 587-593 also demonstrated the anxiolytic effects of MGS0039, a potent antagonist of group II mGlu receptors ($mGlu_2$ and $mGlu_3$), by use of a conditioned fear stress (CFS) model, which represents emotional abnormality, including anxiety. The CFS model reflects psychological stress without physical stimuli and is useful in predicting the clinical efficacy of anxiolytic drugs. In these studies, MGS0039 significantly decreased freezing behavior, as did diazepam and fluvoxamine, indicating the anxiolytic-like potential of MGS0039. The $mGlu_{2/3}$ receptors inhibit neurotransmitter release as autoreceptors located on glutamatergic terminals and treatment with $mGlu_{2/3}$ antagonists such as MGS0039 in vivo lead to an increase in extracellular glutamate. Therefore, the moderate elevation of glutamate levels in specific areas of the brain by MGS0039 may cause the anxiolytic-like effects seen in the CFS model. These results suggest that the blockade of $mGlu_{2/3}$ with MGS0039 may be effective in the treatment of anxiety disorders.

F. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

G. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of antidepressants, Alzheimer's disease medications, and anxiolytics.

The compound of Formula (I) can be combined with the following antidepressants, but not limited to: Selective serotonin reuptake inhibitors (SSRIs) such as citalopram, dapoxetine, escitalopram, fluoxetine, fluvoxamine, indalpine, paroxetine, sertraline, and zimelidine; Serotonin-norepinephrine reuptake inhibitors (SNRIs) such as venlafaxine, desvenlafaxine, duloxetine, milnacipran, levomilnacipran, and sibutramine; Noradrenergic and specific serotonergic antidepressants (NaSSAs) or tetracyclic antidepressants (TeCAs) such as aptazapine, esmirtazapine, mianserin, mirtazapine, and setiptiline; Serotonin antagonist and reuptake inhibitors (SARIs) such as etoperidone, lorpiprazole, mepiprazole, nefazodone, trazodone, vilazodone, and niaprazine; Norepinephrine-dopamine reuptake inhibitors (NDRIs) such as armodafinil, bupropion, desoxypipradrol, dexmethylphenidate, methylphenidate, modafinil, prolintane, and tametraline; Serotonin-norepinephrine-dopamine reuptake inhibitors (SNDRIs) such as nefopam, amitifadine, tesofensine, and tedatioxetine; Tricyclic antidepressants (TCAs) such as clomipramine, desipramine, imipramine, dibenzepin, lofepramine, nortriptyline, protriptyline, amitriptyline, amitriptylinexide, amoxapine, butriptyline, demexiptiline, dimetacrine, dosulepin, doxepin, imipraminoxide, melitracen, metapramine, nitroxazepine, noxiptiline, pipofezine, propizepine, quinupramine, amineptine, iprindole, opipramol, tianeptine, and trimipramine; and Negative allosteric modulators of metabotropic glutamate receptor 5 ($mGlu_5$) such as mavoglurant, basimglurant, dipraglurant, STX107, and N-(5-fluoropyridin-2-yl)-6-methyl-4-(pyrimidin-5-yloxy)picolinamide.

The compound of Formula (I) can be combined with the following Alzheimer's disease medications, but not limited to: Acetylcholinesterase inhibitors such as tacrine, rivastigmine, galantamine, donepezil, edrophonium, physostigmine, pyridostigmine, ambenonium, rivastigmine, ladostigil, and ungeremine; and NMDA receptor antagonists such as memantine, amantadine, delucemine, and ketamine.

The compound of Formula (I) can be combined with the following anxiolytics, but not limited to: buspirone, tandospirone, gepirone, adaptol, afobazole, hyroxyzine, validol, melatonin, and benzodiazepines such as alprazolam, chlordiazepoxide, clonazepam, diazepam, etizolam, lorazepam, oxazepam, and tofisopam.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

5. Examples

All NMR spectra were recorded on a 400 MHz AMX Bruker NMR spectrometer. $^1H$ chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

a. Abbreviations

Celite® is diatomaceous earth;

$CHCl_3$ is chloroform;

DCM for dichloromethane;

DMF is N,N-dimethylformamide;
DMSO is dimethylsulfoxide;
eq, eq., or equiv is equivalent(s);
EtOAc is ethyl acetate;
h or hr is hours;
HPLC is high performance liquid chromatography;
IPA is isopropyl alcohol;
LCMS is liquid chromatography mass spectrometry;
MeCN is acetonitrile;
MeOH is methanol;
min or min. is minute(s);
mw is microwave irradiation;
$Pd(dppf)Cl_2$ is [1,1'-Bis(diphenylphosphino)ferrocene]dichloropalladium(II);
rt. RT, or r.t. is room temperature;
sat. is saturated;
TFA is trifluoroacetic acid;
THF is tetrahydrofuran.

b. Preparation of Intermediates

Intermediate Example 1

6-Bromo-7-fluoroquinazolin-4(3H)-one

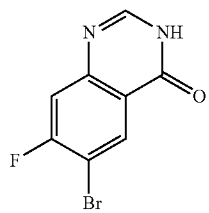 [SMILES: O=c1[nH]cnc2cc(F)c(Br)cc12]

A mixture of 2-amino-5-bromo-4-fluorobenzoic acid (100 mg, 0.43 mmol) and formamide (0.17 mL, 4.3 mmol) was heated to 150° C. After 17 h, the reaction mixture was cooled to rt and purified via normal phase column chromatography on silica gel (gradient 0-50% EtOAc in hexanes) to yield 6-bromo-7-fluoroquinazolin-4(3H)-one (44 mg, 42%). ES-MS $[M+H]^+$: 244.8, $^1H$ NMR (400 MHz, $(CD_3)_2SO$) δ 8.35 (d, J=7.7 Hz, 1H), 8.18 (s, 1H), 7.67 (d, J=9.8 Hz, 1H).

Intermediate Example 2

7-Fluoro-6-(4-fluorophenyl)quinazolin-4(3H)-one

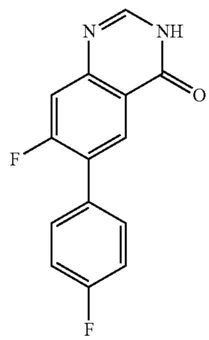 [SMILES: O=c1[nH]cnc2cc(F)c(-c3ccc(F)cc3)cc12]

A mixture of 6-bromo-7-fluoroquinazolin-4(3H)-one (106 mg, 0.44 mmol), 4-fluorophenylboronic acid (129 mg, 0.92 mmol), $Pd(dppf)Cl_2$ (36 mg, 0.04 mmol), $Na_2CO_3$ (114 mg, 1.1 mmol), 1,4-dioxane (2 mL), and $H_2O$ (1 mL) was heated to 100° C. After 4 h, the mixture was cooled to rt, diluted with $H_2O$, and extracted with $CHCl_3$:IPA (3:1). The combined organic fractions were passed through a phase separator, concentrated, and purified via normal phase column chromatography on silica gel (gradient 0-100% EtOAc in hexanes) to yield 7-fluoro-6-(4-fluorophenyl)quinazolin-4(3H)-one (79 mg, 69%). ES-MS $[M+H]^+$: 258.9, $^1H$ NMR (400 MHz, $(CD_3)_2SO$) δ 8.13 (s, 1H), 8.10 (d, J=9.0 Hz, 1H), 7.69-7.60 (m, 2H), 7.42 (d, J=12.0 Hz, 1H), 7.37-7.30 (m, 2H).

The compounds shown in Table 1 may be prepared similarly to the compound described above, with appropriate starting materials.

TABLE 1

| Structure | Name | $^1H$-NMR and/or ES-MS $[M + H]^+$ |
| --- | --- | --- |
| 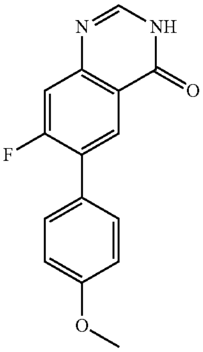 [SMILES: COc1ccc(-c2cc3c(=O)[nH]cnc3cc2F)cc1] | 7-Fluoro-6-(4-methoxyphenyl) quinazolin-4(3H)-one | ES-MS $[M + H]^+$: 270.9, $^1H$ NMR (400 MHz $(CD_3)_2SO$) δ 8.18-8.11 (m, 2H), 7.61-7.52 (m, 3H), 7.12-7.04 (m, 2H), 3.82 (s, 3H). |
| 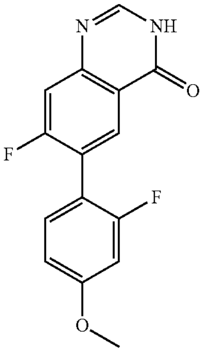 [SMILES: COc1ccc(-c2cc3c(=O)[nH]cnc3cc2F)c(F)c1] | 7-Fluoro-6-(2-fluoro-4-methoxyphenyl) quinazolin-4(3H)-one | ES-MS $[M + H]^+$: 288.9, $^1H$ NMR (400 MHz $(CD_3)_2SO$) δ 8.17 (s, 1H), 8.09 (d, J = 8.1 Hz, 1H), 7.57 (d, J = 11.0 Hz, 1H), 7.47 (dd, J = 8.7, 8.7 Hz, 1H), 7.05-6.90 (m, 2H), 3.84 (s, 3H). |

Intermediate Example 3

6-Bromo-7-((1-methyl-1H-pyrazol-3-yl)methoxy) quinazolin-4(3H)-one

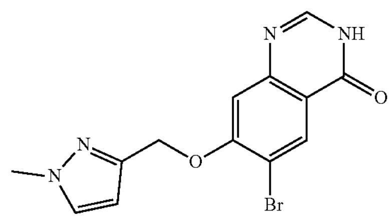 [SMILES: Cn1ccc(COc2cc3nc[nH]c(=O)c3cc2Br)n1]

To a solution of (1-methyl-1H-pyrazol-3-yl)methanol (46 mg, 0.41 mmol) in THF (1 mL) was added NaH (10 mg, 0.41 mmol). After 10 min, a solution of 6-bromo-7-fluoroquinazolin-4(3H)-one (50 mg, 0.21 mmol) in THF (1 mL) was added dropwise. The mixture was heated to 130° C. After 4 h, the mixture was cooled to rt, quenched with $H_2O$, and extracted with $CHCl_3$:IPA (3:1). The organic fractions were combined, passed through a phase separator, concentrated, and purified via reverse phase HPLC (gradient 5-60% MeCN in $H_2O$ ($H_2O$ modified with 0.05% $NH_4OH$ per 1 L $H_2O$) to yield 6-bromo-7-((1-methyl-1H-pyrazol-3-yl)methoxy)quinazolin-4(3H)-one (31 mg, 69%). ES-MS $[M+H]^+$: 337.0, $^1H$ NMR (400 MHz $(CD_3)_2SO$) δ 8.19 (s, 1H), 8.10 (s, 1H), 7.69 (d, J=2.2 Hz, 1H), 7.40 (s, 1H), 6.36 (d, J=2.2 Hz, 1H), 5.24 (s, 2H), 3.84 (s, 3H).

c. Commercial Starting Materials

TABLE 2

| Chemdraw Name | CAS | Vendor |
|---|---|---|
| 2-amino-5-bromo-4-fluorobenzoic acid | 143945-65-7 | Combi-Blocks, Inc. |
| formamide | 75-12-7 | Oakwood Products, Inc. |
| (4-fluorophenyl)boronic acid | 1765-93-1 | Combi-Blocks, Inc. |
| (2-fluoro-4-methoxyphenyl)boronic acid | 62101-31-7 | Combi-Blocks, Inc. |
| (4-methoxyphenyl)boronic acid | 5720-07-0 | Combi-Blocks, Inc. |
| (1-methyl-1H-pyrazol-3-yl)methanol | 84547-62-6 | Combi-Blocks, Inc. |
| (1-methyl-1H-pyrazol-5-yl)methanol | 84547-61-5 | Ambeed |
| (6,7-dihydro-4H-pyrazolo[5,1-c][1,4]oxazin-2-yl)methanol | 623565-58-2 | Enamine |
| (2,4-difluorophenyl)boronic acid | 144025-03-6 | Sigma-Aldrich Corporation |
| 1-methyl-3-(4,4,5,5-tetramethyl-1,3,2-dioxaborolan-2-yl)-1H-pyrrole | 953040-54-5 | Combi-Blocks, Inc. |

d. Preparation of Representative Compounds

Example 1

6-(4-Fluorophenyl)-7-((1-methyl-1H-pyrazol-3-yl)methoxy)quinazolin-4(3H)-one (Compound 1)

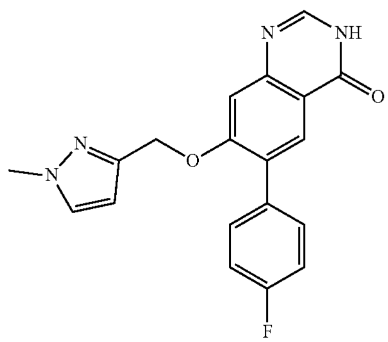 [SMILES: Cn1ccc(COc2cc3nc[nH]c(=O)c3cc2-c2ccc(F)cc2)n1]

To a solution of (1-methyl-1H-pyrazol-3-yl)methanol (9 mg, 0.08 mmol) in THF (1 mL) was added NaH (2 mg, 0.08 mmol). After 10 min, a solution of 7-fluoro-6-(4-fluorophenyl)quinazolin-4(3H)-one (11 mg, 0.04 mmol) in THF (1 mL) was added dropwise. The mixture was heated to 130° C. After 4 h, the mixture was cooled to rt, quenched with $H_2O$, and extracted with $CHCl_3$:IPA (3:1). The combined organic fractions were passed through a phase separator, concentrated, and purified via reverse phase HPLC (gradient 10-50% MeCN in $H_2O$ ($H_2O$ modified with 0.05% $NH_4OH$ per 1 L $H_2O$)) to yield 6-(4-fluorophenyl)-7-((1-methyl-1H-pyrazol-3-yl)methoxy)quinazolin-4(3H)-one (1.2 mg, 8%). ES-MS $[M+H]^+$: 351.1, $^1H$ NMR (400 MHz, $(CD_3)_2SO$) δ 8.08 (s, 1H), 7.92 (s, 1H), 7.65 (d, J=2.2 Hz, 1H), 7.63-7.57 (m, 2H), 7.38 (s, 1H), 7.29-7.20 (m, 2H), 6.27 (d, J=2.2 Hz, 2H), 5.20 (s, 3H), 3.81 (s, 3H).

Example 2

6-(2,4-Difluorophenyl)-7-((1-methyl-1H-pyrazol-3-yl)methoxy)quinazolin-4(3H)-one (Compound 5)

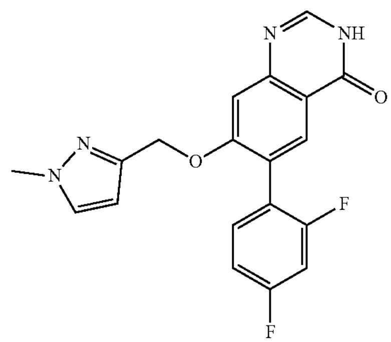 [SMILES: Cn1ccc(COc2cc3nc[nH]c(=O)c3cc2-c2ccc(F)cc2F)n1]

A mixture of 6-bromo-7-((1-methyl-1H-pyrazol-3-yl)methoxy)quinazolin-4(3H)-one (15 mg, 0.05 mmol), 2,4-difluorophenylboronic acid (15 mg, 0.10 mmol), Pd(dppf)$Cl_2$ (4 mg, 0.005 mmol), $Na_2CO_3$ (12 mg, 0.11 mmol), 1,4-dioxane (0.5 mL), and $H_2O$ (0.10 mL) was heated to 100° C. After 3 h, the mixture was cooled to rt, diluted with $H_2O$, and extracted with $CHCl_3$:IPA (3:1). The combined organic fractions were passed through a phase separator, concentrated, and purified by reverse phase HPLC (gradient 10-50% MeCN in $H_2O$ ($H_2O$ modified with 0.05% $NH_4OH$ per 1 L $H_2O$)) to yield 6-(2,4-difluorophenyl)-7-((1-methyl-1H-pyrazol-3-yl)methoxy)quinazolin-4(3H)-one (9 mg, 53%). %). ES-MS $[M+H]^+$: 369.0, $^1H$ NMR (400 MHz, $(CD_3)_2SO$) δ 8.10 (s, 1H), 7.89 (s, 1H), 7.63 (d, J=2.2 Hz, 1H), 7.55-7.45 (m, 1H), 7.39 (s, 1H), 7.32 (ddd, J=10.6, 9.8, 2.5 Hz, 1H), 7.15 (ddd, J=8.6, 8.6, 2.7 Hz, 1H), 6.16 (d, J=2.2 Hz, 1H), 5.17 (s, 2H), 3.80 (s, 3H).

The compounds shown in Table 3 may be prepared using the preceding methods (see Examples 1 and 2) with the appropriate starting materials.

TABLE 3
| No. | Name | Structure | Example[1] | ES-MS [M + 1]+ |
|---|---|---|---|---|
| 1 | 6-(4-fluorophenyl)-7-((1-methyl-1H-pyrazol-3-yl)methoxy)quinazolin-4(3H)-one | 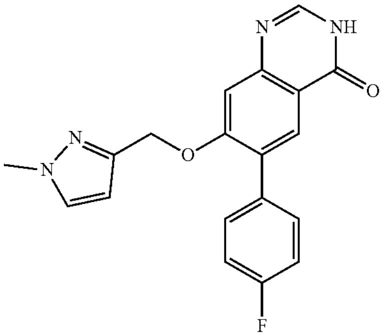 [SMILES: Cn1ccc(COc2cc3nc[nH]c(=O)c3cc2-c2ccc(F)cc2)n1] | 1 | 351.1 |
| 2 | 6-(4-fluorophenyl)-7-((1-methyl-1H-pyrazol-5-yl)methoxy)quinazolin-4(3H)-one | 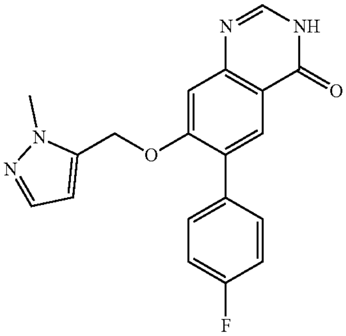 [SMILES: Cn1nccc1COc1cc2nc[nH]c(=O)c2cc1-c1ccc(F)cc1] | 1 | 351.1 |
| 3 | 7-((6,7-dihydro-4H-pyrazolo[5,1-c][1,4]oxazin-2-yl)methoxy)-6-(4-fluorophenyl)quinazolin-4(3H)-one | 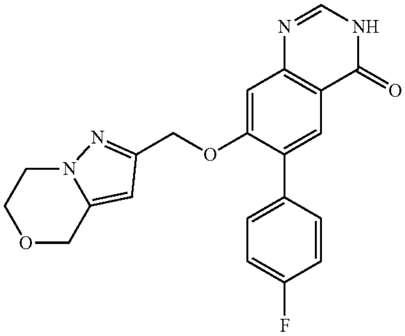 [SMILES: O=c1[nH]cnc2cc(OCc3cc4n(n3)CCOC4)c(-c3ccc(F)cc3)cc12] | 1 | 393.1 |
| 4 | 6-(2-fluoro-4-methoxyphenyl)-7-((1-methyl-1H-pyrazol-3-yl)methoxy)quinazolin-4(3H)-one | 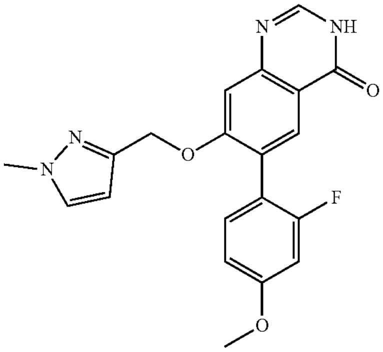 [SMILES: COc1ccc(-c2cc3c(=O)[nH]cnc3cc2OCc2ccn(C)n2)c(F)c1] | 1 | 381.1 |

TABLE 3-continued

| No. | Name | Structure | Example[1] | ES-MS $[M + 1]^+$ |
|---|---|---|---|---|
| 5 | 6-(2,4-difluorophenyl)-7-((1-methyl-1H-pyrazol-3-yl)methoxy)quinazolin-4(3H)-one | 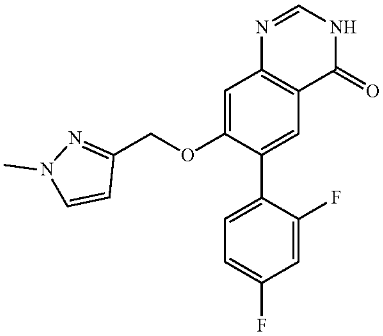 [SMILES: Cn1ccc(COc2cc3nc[nH]c(=O)c3cc2-c2ccc(F)cc2F)n1] | 2 | 369 |
| 6 | 7-((1-methyl-1H-pyrazol-3-yl)methoxy)-6-(1-methyl-1H-pyrrol-3-yl)quinazolin-4(3H)-one | 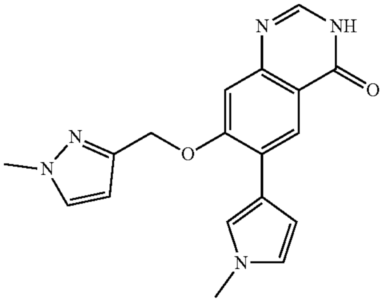 [SMILES: Cn1ccc(-c2cc3c(=O)[nH]cnc3cc2OCc2ccn(C)n2)c1] | 2 | 336.1 |
| 7 | 6-(4-methoxyphenyl)-7-((1-methyl-1H-pyrazol-3-yl)methoxy)quinazolin-4(3H)-one | 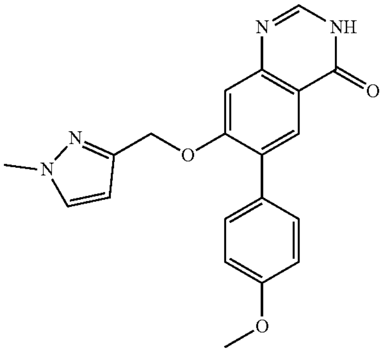 [SMILES: COc1ccc(-c2cc3c(=O)[nH]cnc3cc2OCc2ccn(C)n2)cc1] | 1 | 363.1 |
| 8 | 7-((6,7-dihydro-4H-pyrazolo[5,1-c][1,4]oxazin-2-yl)methoxy)-6-(4-methoxyphenyl)quinazolin-4(3H)-one | 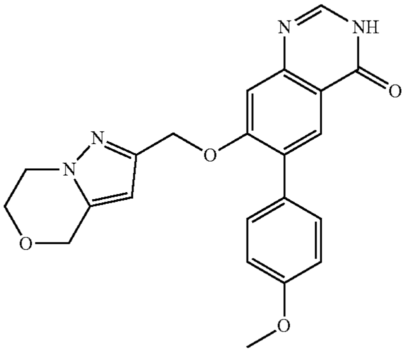 [SMILES: COc1ccc(-c2cc3c(=O)[nH]cnc3cc2OCc2cc3n(n2)CCOC3)cc1] | 1 | 405.1 |

[1]Prepared according to Example 1 or Example 2 (see preceding subsection "d. Preparation of Representative Compounds") with appropriate starting materials.

Biological Activity

A. Cell Lines Co-Expressing mGlu and GIRK

Human embryonic kidney (HEK-293) cell lines stably co-expressing human $mGlu_2$ and G protein-coupled inwardly rectifying potassium (GIRK) channels, or human $mGlu_3$ and GIRK, were used for in vitro evaluation of compound activity through thallium flux assays.

B. Cell-Based Tl Flux Assay of mGlu and GIRK Activity

The day before the assay, cells from cell lines co-expressing human $mGlu_2$ or $mGlu_3$ and GIRK, as described above, were plated in black-walled, clear-bottomed, amine-coated 384-well plates in 20 μL of assay medium (DMEM containing 10% FBS, 1 M HEPES, 100 mM sodium pyruvate) at a density of 15,000 cells/well and stored at 37° C. in the presence of 5% $CO_2$. On the day of the assay, medium was removed and replaced with assay buffer (Hanks balanced salt solution, 20 mM HEPES, 4.16 mM sodium bicarbonate, pH 7.2) containing 0.328 μM FluoZin-2 AM dye. The dye was initially made up as a 2.85 mM stock in DMSO and diluted 1:1 with 10% pluronic acid before adding to the buffer. Cells were then incubated for one hour at room temperature. After dye-loading, excess extracellular dye was removed by exchanging the dye solution with assay buffer resulting in 20 μL of buffer in each well. After a ten-minute rest period, cell plates were loaded into a Hamamatsu μCell kinetic imaging plate reader to monitor fluorescence using 470 nm excitation and 540 nm emission settings.

After collection of baseline fluorescence, 20 μL of compound solution prepared as a concentration response series in assay buffer was added. The concentration series was created from a 10 mM DMSO compound stock by performing a 1:3 serial dilution in DMSO followed by a 1:167 dilution of each DMSO solution in buffer. This results in a 10-point curve ranging from 30 μM down to 1.5 nM final concentration in the assay. Two minutes and twenty seconds after the compound addition, 10 μL of thallium buffer (125 mM sodium bicarbonate, 12 mM thallium sulfate, 1 mM magnesium sulfate, 1.8 mM calcium sulfate, 5 mM glucose, 10 mM HEPES, pH 7.2) containing an $EC_{80}$ glutamate concentration (a concentration resulting in a response 80% of a maximally effective glutamate concentration) was added to the wells containing compound. Multiple reference wells containing no compound received either no glutamate (for a baseline reference), $EC_{80}$ glutamate, or $EC_{max}$ glutamate (for normalization to maximum response). Signal was monitored an additional 2.5 minutes after the glutamate addition. Fluorescence was measured throughout the experiment at a frequency of 1 measurement per every 2 seconds before the glutamate addition and a frequency of 1 measurement per every 1 second after the glutamate addition. Each compound concentration series occurred one time in each plate, and replicates from two or three plates were used in each experimental run. Thallium solutions were handled and disposed of according to guidelines from the Vanderbilt University Chemical Safety department.

Data were normalized using a static ratio function ($F/F_0$) by dividing every fluorescent measurement by the initial fluorescent value for the corresponding well. The increase in signal resulting from the glutamate/thallium addition of the second add was measured by determining the slope from 3 seconds to 13 seconds after the addition. The average of all baseline slopes (no compound, no glutamate) was determined and this value was subtracted from all other slope values. The average of all $EC_{max}$ slopes was determined and this value was used to normalize the baseline-corrected slopes to a percent max value (% $E_{max}$). The % $E_{max}$ values for each compound series were plotted versus the log of the concentration and fit to a 4-parameter logistical equation with no fixed parameters.

Potency is reported as the $IC_{50}$ resulting from the curve fit. For compounds that do not plateau and do not inhibit the glutamate response to less than 20% of the $E_{max}$, a low potency value of >10,000 nM is assigned. For those that do not inhibit lower than 60% of the $E_{max}$ at 30 μM compound, a >30,000 nM potency is assigned. If a compound reaches a plateau of inhibition above 20% and below 60% $E_{max}$, the $IC_{50}$ from the curve fit is reported and a category of "partial NAM" is assigned.

C. Activity of Compounds in a mGlu GIRK Cell-Based Tl Flux Assay

Activity ($IC_{50}$) was determined in the mGlu GIRK cell-based Tl flux assay as described above and the data are shown in Table 4.

TABLE 4

| Compound | Human $mGlu_2$ GIRK $IC_{50}$ (nM) | Human $mGlu_3$ GIRK $IC_{50}$ (nM) |
|---|---|---|
| 1 | 108 | >30,000 |
| 2 | 410 | >30,000 |
| 3 | 456 | >30,000 |
| 4 | 99.7 | >30,000 |
| 5 | 52.6 | >30,000 |
| 6 | 5870 | >30,000 |
| 7 | 103 | >30,000 |
| 8 | 147 | >30,000 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I), or a pharmaceutically acceptable salt thereof, (I)

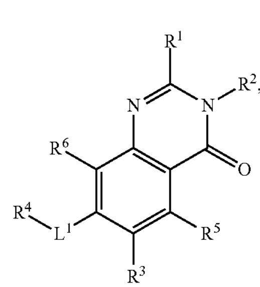

wherein:

$L^1$ is a $C_{1-6}$alkylene or $C_{1-6}$fluoroalkylene, wherein optionally 1 methylene group in the alkylene or fluoroalkylene of $L^1$ is independently replaced with —O—;

$R^1$ is hydrogen or $C_{1-6}$alkyl;

$R^2$ is hydrogen or $C_{1-6}$alkyl;

$R^3$ is phenyl or pyrrolyl, wherein $R^3$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$ haloalkyl;

$R^4$ is phenyl,

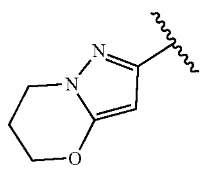

pyridinyl, imidazolyl, thiazolyl, pyrazolyl, or oxazolyl, wherein $R^4$ is unsubstituted or substituted with 1, 2, 3, or 4 substituents independently selected from the group consisting of $C_{1-4}$alkyl, halogen, cyano, $C_{1-2}$haloalkyl, —$OC_{1-4}$alkyl, and —$OC_{1-2}$haloalkyl; and $R^5$ and $R^6$ are each independently hydrogen, $C_{1-4}$alkyl, halogen, cyano, $C_{1-2}$haloalkyl, —$OC_{1-4}$alkyl, or —$OC_{1-2}$haloalkyl.

2. The compound of claim 1, or a pharmaceutically acceptable salt thereof, wherein $L^1$ is

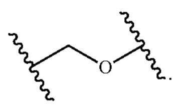 [SMILES: *CO*]

3. The compound of claim 1, or a pharmaceutically acceptable salt thereof, wherein $R^2$ is hydrogen.

4. The compound of claim 1, or a pharmaceutically acceptable salt thereof, wherein $R^4$ is

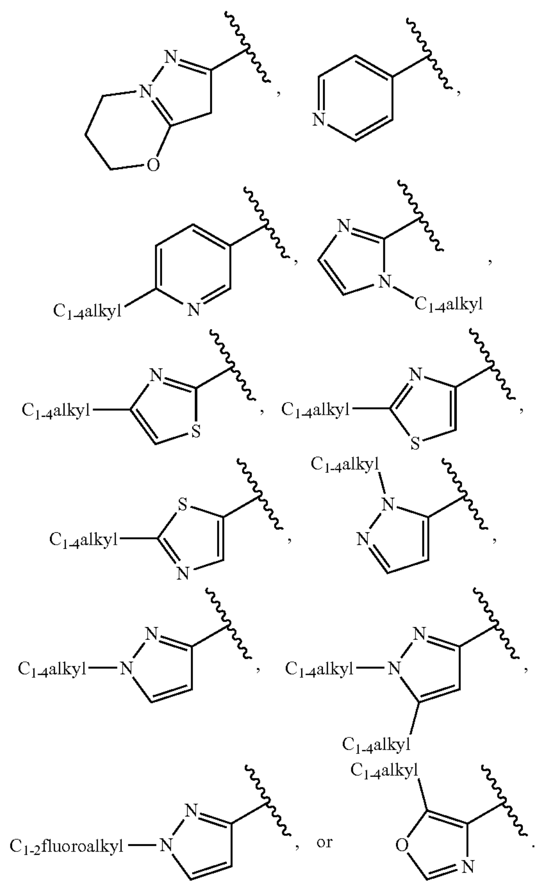

5. The compound of claim 4, or a pharmaceutically acceptable salt thereof, wherein $R^4$ is

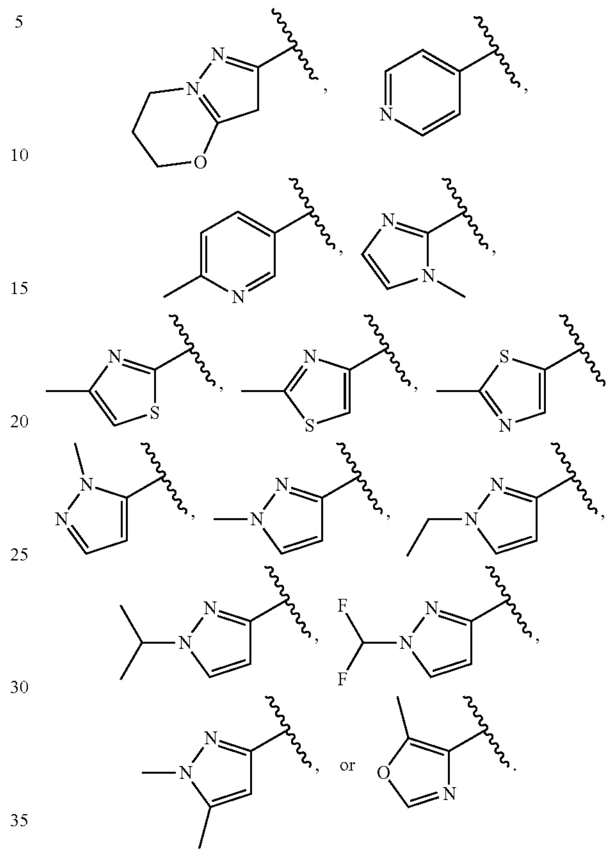

6. The compound of claim 1, or a pharmaceutically acceptable salt thereof, wherein $R^3$ is

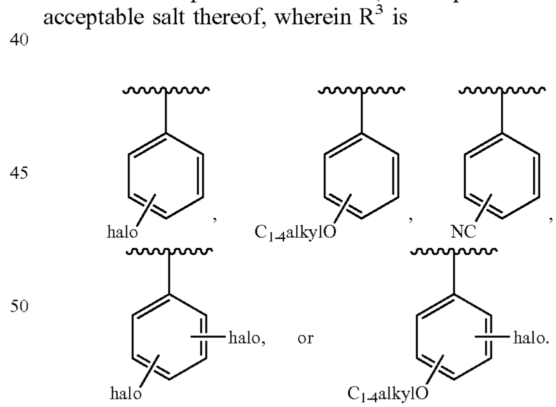

7. The compound of claim 6, or a pharmaceutically acceptable salt thereof, wherein $R^3$ is

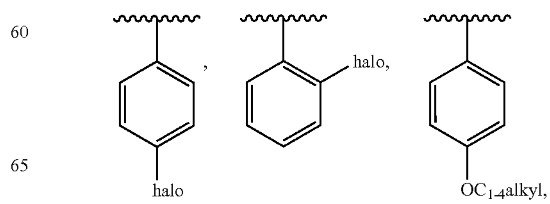

-continued

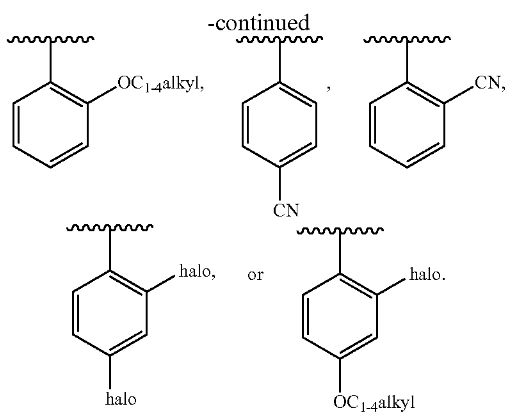

8. The compound of claim 7, or a pharmaceutically acceptable salt thereof, wherein $R^3$ is

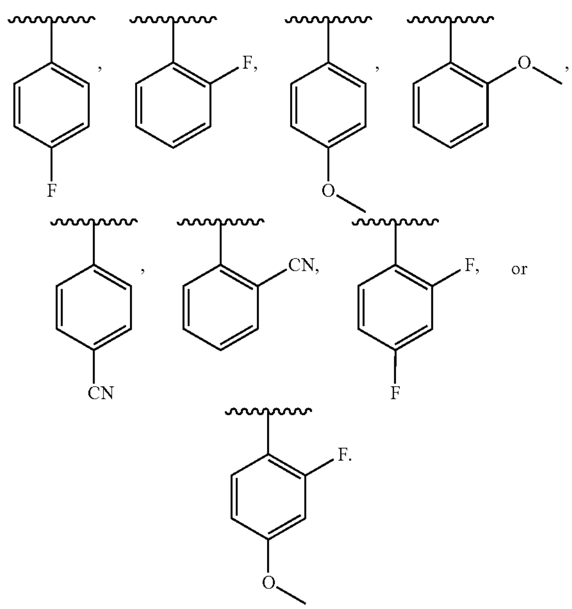

9. The compound of claim 1, or a pharmaceutically acceptable salt thereof, wherein $R^3$ is

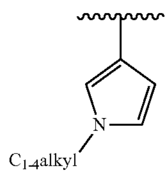

10. The compound of claim 1, or a pharmaceutically acceptable salt thereof, wherein $R^5$ and $R^6$ are each independently selected from the group consisting of hydrogen, $C_{1-4}$alkyl, and halogen.

11. The compound of claim 1, or a pharmaceutically acceptable salt thereof, wherein $R^5$ and $R^6$ are each hydrogen.

12. The compound of claim 1, or a pharmaceutically acceptable salt thereof, wherein $R^1$ is hydrogen.

13. The compound of claim 1, or a pharmaceutically acceptable salt thereof, wherein the compound is a compound of formula (Ia):

(Ia)

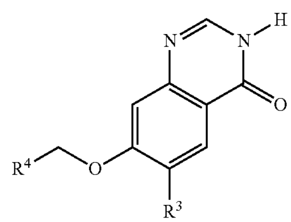

14. The compound of claim 1, selected from the group consisting of:

6-(4-fluorophenyl)-7-((1-methyl-1H-pyrazol-3-yl)methoxy)quinazolin-4(3H)-one;

6-(4-fluorophenyl)-7-((1-methyl-1H-pyrazol-5-yl)methoxy)quinazolin-4(3H)-one;

7-((6,7-dihydro-4H-pyrazolo[5,1-c][1,4]oxazin-2-yl)methoxy)-6-(4-fluorophenyl)quinazolin-4(3H)-one;

6-(2-fluoro-4-methoxyphenyl)-7-((1-methyl-1H-pyrazol-3-yl)methoxy)quinazolin-4(3H)-one;

6-(2,4-difluorophenyl)-7-((1-methyl-1H-pyrazol-3-yl)methoxy)quinazolin-4(3H)-one;

7-((1-methyl-1H-pyrazol-3-yl)methoxy)-6-(1-methyl-1H-pyrrol-3-yl)quinazolin-4(3H)-one;

6-(4-methoxyphenyl)-7-((1-methyl-1H-pyrazol-3-yl)methoxy)quinazolin-4(3H)-one; and 7-((6, 7-dihydro-4H-pyrazolo[5,1-c][1,4]oxazin-2-yl)methoxy)-6-(4-methoxyphenyl)quinazolin-4(3H)-one;

or a pharmaceutically acceptable salt thereof.

15. A pharmaceutical composition comprising the compound of claim 1, or a pharmaceutically acceptable salt thereof, and a pharmaceutically acceptable carrier.

* * * * *